(12) United States Patent
Imhof et al.

(10) Patent No.: US 7,393,651 B2
(45) Date of Patent: Jul. 1, 2008

(54) CONFLUENCE REGULATED ADHESION MOLECULES USEFUL IN MODULATING VASCULAR PERMEABILITY

(75) Inventors: Beat Albert Imhof, Conches (CH); Michel Aurrand-Lions, Geneva (CH)

(73) Assignee: Laboratoires Serono S.A., Coinsins (CH)

( * ) Notice: Subject to any disclaimer, the term of this patent is extended or adjusted under 35 U.S.C. 154(b) by 0 days.

(21) Appl. No.: 11/025,834

(22) Filed: Dec. 30, 2004

(65) Prior Publication Data

US 2005/0266426 A1 Dec. 1, 2005

Related U.S. Application Data

(63) Continuation of application No. 09/524,531, filed on Mar. 13, 2000, now abandoned.

(30) Foreign Application Priority Data

Mar. 11, 1999 (EP) .................................. 99200746

(51) Int. Cl.
*G01N 33/53* (2006.01)
*C07K 14/00* (2006.01)
(52) U.S. Cl. ......................................... 435/7.1; 530/353
(58) Field of Classification Search ........................ None
See application file for complete search history.

(56) References Cited

U.S. PATENT DOCUMENTS

| 6,469,155 B1 | 10/2002 | Fiume et al. |
| 6,635,468 B2 | 10/2003 | Ashkenazi et al. |
| 6,930,172 B2 * | 8/2005 | Ferrara et al. ............. 530/387.1 |
| 2005/0136060 A1 | 6/2005 | Imhof et al. |

FOREIGN PATENT DOCUMENTS

| WO | WO 98/24897 A1 | 6/1998 |
| WO | WO 98/42739 A2 | 10/1998 |
| WO | WO 99/06551 A2 | 2/1999 |
| WO | WO 00/36102 A2 | 6/2000 |

OTHER PUBLICATIONS

Aurrand-Lions, M. et al. "Heterogeneity of endothelial junctions is reflected by differential expression and specific subcellular localization of the three JAM family members" *Blood*, Dec. 15, 2001, pp. 3699-3707, vol. 98, No. 13.
Skolnick, J. et al. "From genes to protein structure and function: novel applications of computational approaches in the genomic era" *Trends in Biotech*, Jan. 2000, pp. 34-39, vol. 18, No. 1.
Attwood, T. K. "The Babel of Bioinformatics" *Science*, Oct. 20, 2000, pp. 471-473, vol. 290.

Database EMBL (Online), Accession No. AI154320, Oct. 1, 1998, Marra, M. "EST: Mouse mammary gland cDNA clone Image:1447499", XP-002144155.
Database EMBL (Online), Accession No. AI1663309, May 11, 1999, Marra, M. "EST: *M. musculus* cDNA clone Image:1970215 similar to Junctional Adhesion Molecule", XP-002144156.
Database EMBL (Online), Accession No. AW162934, Nov. 11, 1999, Hillier, L. "EST: *H. sapiens* cDNA clone Image:2783568 similar to Junctional Adhesion Molecule", XP-002144157.
Martin-Padura, I. et al. "Junctional Adhesion Molecule, a Novel Member of the Immunoglobulin Superfamily That Distributes at Intercellular Junctions and Modulates Monocyte Transmigration" *J. Cell. Biol.*, Jul. 13, 1998, pp. 117-127, vol. 142, No. 1.
Heath, J.K. et al. "The human A33 antigen is a transmembrane glycoprotein and a novel member of the immunoglobulin superfamily" *Proc. Natl. Acad. Sci.* USA, Jan. 21, 1997, pp. 469-474, vol. 94, No. 2.
Jermutus, L. et al. "Recent advances in producing and selecting functional proteins by using cell-free translation" *Current Opinion in Biotechnology*, Oct. 1998, pp. 534-548, vol. 9, No. 5.
Lamagna, C. et al. "Dual Interaction of JAM-C with JAM-B and $\alpha_M\beta_2$ Integrin: Function in Junctional Complexes and Leukocyte Adhesion" *Molecular Biology of the Cell*, Oct. 2005, pp. 4992-5003, vol. 16, No. 10.
Dufresne, G. et al. "Genetic sequences: how are they patented?" *Nature Biotechnology*, Feb. 2004, pp. 231-232, vol. 22, No. 2.
Hanes, J. et al. "In vitro selection and evolution of functional proteins by using ribosome display" *Proc. Natl. Acad. Sci.* USA, May 13, 1997, pp. 4937-4942, vol. 94, No. 10.
Webber, C. et al. "Genes and homology" *Current Biology*, May 4, 2004, pp. R332-333, vol. 14, No. 9.
Lewin, R. "When Does Homology Mean Something Else?" *Science*, Sep. 25, 1987, p. 1570, vol. 237, No. 4822.
Sczakiel, G. The design of antisense RNA *Antisense Nucleic Acid Drug Dev.*, Aug. 1997, pp. 439-444, vol. 7, No. 4, abstract only.
Johnstone, C. N. et al. "Characterization of mouse A33 antigen, a definitive marker for basolateral surfaces of intestinal epithelial cells" *Am. J. Physiol Gastrointest Liver Physiol.*, Sep. 2000, pp. G500-510, vol. 279, No. 3.
Lamagna, C. et al. "Antibody against Junctional Adhesion Molecule-C Inhibits Angiogenesis and Tumor Growth" *Cancer Res*, Jul. 1, 2005, pp. 5703-5710, vol. 65, No. 13.
Orlova, V. V. et al. "Junctional adhesion molecule-C regulates vascular endothelial permeability by modulating VE-cadherin-mediated cell-cell contacts" *The Journal of Experimental Medicine*, Nov. 27, 2006, pp. 2703-2714, vol. 203, No. 12.

* cited by examiner

*Primary Examiner*—Maher M Haddad
(74) *Attorney, Agent, or Firm*—Saliwanchik, Lloyd & Saliwanchik

(57) ABSTRACT

The invention relates to new polypeptide in isolated form belonging to a subfamily of the human Immunoglobulin Superfamily, which polypeptide shows at least 70% sequence homology with the amino acid sequence of the murine Confluency Regulated Adhesion Molecules 1 or 2 (CRAM-1 or CRAM-2) as depicted in FIG. 3 upper and second row, respectively, and antibodies thereto as well as their use in treatment of inflammation and tumors.

30 Claims, 38 Drawing Sheets

FIG. 1A

Figure 2A:
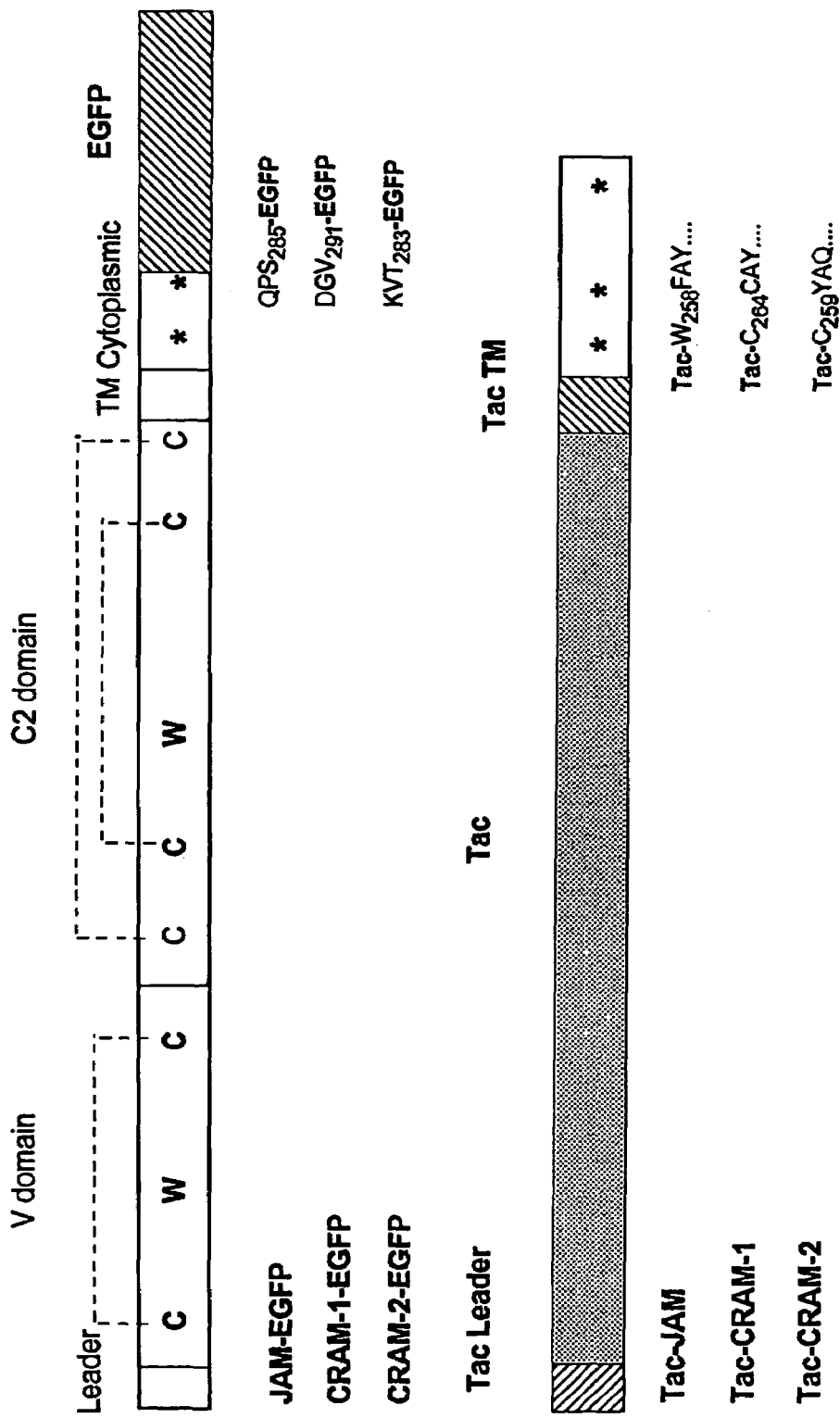

```
>muCRAM-1
CAGACATTCCCCTCGACATGGGCGCTGAGCCGGCGGCTGCGACTTCGACTGTACGCGCGGCTGCCT
CACTTCTTCCTGCTGCTCAGGGCTGCATGATAGAGGCAGTGAATCTCAAATCCAGCAA
CCGAAACCCAGTGTACACAGTGAAGATTGAAGTGTTCTTGCATCATTACGCACTCACAGA
CAAGTGACCCTAGGATTGAAGGAAGAAAATCCAAGATGTGGCCAAACCACATATGTGTATTTGAC
AACAAGATTCAAGGAGACCTGCACAGATGTCGTTTGGAAAAACTTCCCTGAGGATCTG
GAATGTGACACGATCGGATTCAGCCATCTATCGCTGTGAGGTCGTTGCTCTAAATGACCGAAAAG
AAGTTGATGAGATTACCATTGAGTTAATTGTGCAAGTGAAGCCAGTGACCCCTGTCTGCAGAATT
CCAGCCGCTGTACCTGTAGCCAAGACGGCAACACTGCAGTGCCAAGAGAGCGAGGCTATCCCCG
GCCTCACTACAGCTGGTACCGCCAATGATGTGCCACTGCCTACAGATTCCAGAGCCAATCCCAGT
TCCAGAATTCCTCTTTCGGCAGTACTACTGCTTCTGTACAGACAGGCACTCTGGTTTTCAAGTCTGTCCACAAG
GACGACTCTGGGCAGTACTACTGCTTCTGTACAGACAGGTGTTAACTACATCCGGACAGTGA
GGACATGGAAGTCTATGATTACGATTGGGCATCTGCTGTGCTACAGATGACGTGTTATCTGACACCTGGCTGGGAGAGCACATG
TTCTTGCTGTGATGAGAAAGCTATAAGAGCCCAGGGAAGCATGCGTTAACCTGTCGGCTGGGAGAGCACATG
CAAGATGGAGAAAGCTATAAGAGCCCAGGAAGCATGCGTGTTAACCTGTCGGCTGGGAGAGCACATG
GGAGGGTGACTTCAGACACACAAATCGTCTTTGTTATCTGAGCCTGTGAGCTCCTCCTTCGACAAAGCCACC
CAAGTACCTCTGTTGAAGCTGGTCACAGGCTGTGAGACTCCTCCTTCCTTCCTCTTTAACA
CGGGCAGAAGCTTTTTGTTTTGCCCAAAGTTGAAGATGGATGTAGACACAGATTGTTGCTAGCCTGACC
AGCCACAAGAATAAAAGGAAGCCTCGAAGATGGATGTAGACACAGATTGTTGCTAGCCTGACC
TCATTATGGGATTAGGGTGATCTTCAAGGCTGTTGCTGCTTCTCCCAGAGAGAGGCTGAGGCGC
TGGACTGTGTTTTTGCCCCAGCAGCAGCTGTTTAGCTGCCAGGACAACACTGGCAGTGCCCCCAGGAGGCTGAGGCGC
TGGGCTGCAGTAGCAGCAGCAGCAGGCCCTGATGCCTGATGCCTCTGTTGCCTGTTGCCTGATTGGCCAGTACTGTCATTT
AGTGCCTTGCTCCCTGGAGAATGTGTTGACCCACCGTGCCTGTTGCCTGTTGATTGGCCAGTACTGTCATTT
CCATCCTCTGGAGAATGTCTTTGGAATCAGCATTTGCTACTGAAGTGTACTGAAAATCAGAAAGGTGAAATTG
CTTGCTGGGAGAGGGCTCTGACCCAGGAAATGGTACTGAGAGATGTATTTTGATTACTGAAAATTCTATATATAAACT
ACCTGTCTGTCTTAAGTCTGAAATGGTACTGAGAGATGTATTTTGATTACTGAAAATTCTATATATAAACT
AAAATTTAACATTCTAAATTTGCCATACAGTGTTTCAAAAACGTATTTTTTATAAGAAGTCTTTTAAGGAGTTTCTTA
GTAAATATATTGCCATACAGTGTTTCAAAAACGTATTTTTTATAAGAAGTCTTTTAAGGAGTTTCTTA
AGGCTTGGGCTGCTGAATATTCCTTTGTGTTTAATTGGAAAATACCAGTAGTAAAGTTTAGCATTTTCATAAGAAAACTTACT
AGGAGGCTGGCTGAATATTCCTTTGTGTTTAATTGGAAAATACCAGTAGTAAAGTTTAGCATTTTCATAAGAAAACTTACT
CTGTCTGACCACTGTTGCTTAGGAAACCATTAAAGAATTCCAATCTAAAAAAAAAAA
```

FIG. 1B

```
>muCRAM-2
CAGAATTCGGCAGGAGGGTCTGGGGGCGGACCTACGGGTTCTCCTCAAGAGCTAATCTCTGCC
GCCACTCGCTTAGGACCCTGCGGACACCAGTCCTGCGGTCCCGCGTCCCCCTTCCACCCTT
CAAAAGAAGGACTGTCCAGACACTGACATCGGAGAAGAACCTGCGCAGTCGCTGAGACA
CCCCAGACCGAGAGAGACTGACATGCTGGAGAGGCCCAGCCCCTGCCTCCAGGGACCTCTG
CTCCGCCGGGCGGCCCCGGGCGTGCCAAGGCCTCCTGAGCGCTGCTCCTGCGCTCAGTAGG
CAGCCAGCTGCGCCTAGATGCGTAGATGGCGAGGAGCCCCCAAGGCCTCAAGAGCTACACTACT
TGATCGTCGCGCTGAAGAGTTCCAAGAGGCTATTTGGCTTGTGCATCAAAGACCACCGTCAAGAAGTCACA
GTAATAGAGTGTGGACAGAGGCTCTCCTTGTCTTCTATATACGAATCAAAAATCCAGGGACTTTAAAGACCGTG
GAAGAAGTGGACACTCTCCAACTGAGCAAGCCCAGAAGTATTACAAGAGATAAAGTCATGAGAGTATGCTGCTCC
CTGAGATGATAGATTTCAATATACGAATCAAAAATCCAGGCCAGAAGTATTACAAGAGATATAAAGTCATGAGAGTATGCTGCTCC
GTCAGCGCTCGACTGAAGTGCCCACTTCTGTGCCTGAAGTGCAGGAAGTCATGTGAGCTACGATGCCAGATA
TGCTGTGTTCCTGCCTGTGAAGTGCCCACTTCTGTTGGTTAAAGAACGAACTCTGTGGAGCTACGATGCCAGATA
AAGAAGGAACACACAGTCCGGAGAGTATTACTGCAAGTTGCTAGGGAATCACAATGAATCTTCCAA
GGCACACACAGTCCGGAGAGTATTACTGCAAGTTGCTAGGGAATCACAATGAATCTTCCAA
GATGAGCGTGGACAGTCCTATCGCAAGCGGCATCATAGCAGGTTGTGCCTTGTGCTGCCCAGGTGCCCTGGAAGCGAA
TGCAAGTAGATGTCCACATGCTATGCTCAGAGGGCGAAATGATTTCACATGTCATCAACAACCTGTGATTTCTGTA
TGTGCCCTTGCACATGCTATGCTCAGAGGGCGAAATGATTTCACATGTCATCAACAACCTGTGATTTCTGTA
TCCTGCATCTAAAGTCACTACGAAAAATGGAGTTGTGTCAGGAGTTCATCAGGCACACAAATCCTTCCAGAGGGCAG
ATTCCAGTTTGCCTTGCATCTAAAGCTCTGTTTTTGAAGGCATCTGTGTTGACTTGAGTTGAGTTTAGATCTCTAACTCTGTCTTACA
CTTGCAAAGTGATGAAGAAATGAAGAAAATGAAGGGAGTTCAGTTGAGTTTGAGTTTAGATCTCTAACTCTGTCTTACA
ATTTTAAGCAAAGTCTGTTTTGAAGGCATCTGTGTTGACTTGAGTTGAGTTTAGATCTCTAACTCTGTCTTACA
TGTAATATTCTGTTTTTGAAGGCAATATAAAAAAAAAAAAAAAAAAAAAAAAAGAAATGTC
CTAATCCAAGAAGCAAGAATATAAAAAAAAAAAAAAAAAAAAAAAAAAAAAATTC
```

```
MALSRRLRLR LYARLPHFFL LLLFRGCMIE AVNLKSSNRN PVVHEFESVE
  MARSPQGL LMLLLLHYLI VALDYHKANG FSASKDHRQE VTVIEFQEAI

LSCIITHSQT SDPRIEWKKI QDGQTTYVYF DNKIQGDLAG RTDVFGKTSL
LACK-TPKKT TSSRLEWKKV GQG-VSLVYY QQALQGDFKD RAEMID-FNI

RIWNVTRSDS AIYRCEVVAL NDR-KEVDEI TIELIVQVKP VTPVCRIPAA
RIKNVTRSDA GEYRCEVSAP TEQGQNLQED KVMLEVLVAP AVPACEVPTS

VPVGKTATLQ CQESEGYPRP HYSWYRNDVP LPT-DSRANP RFQNSSFHVN
VMTGSVVELR CQDKEGNPAP EYIWFKDGTS LLG-NPKGGT H-NNSSYTNE

SETGTLVFNA VHKDDSGQYY CIASNDAGAA RCEGQDMEVY DLNIAGIIGG
HESGILQFNM ISKMDSGEYY CEARNSVGHR RCPGKRMQVD VLNISGIIAT

VLVVLIVLAV ITMGICCAYR RGCFISSKQD GESYKSPGKH DGVNYIRTSE
VVVVAFVISV CGLGTCYAQR KGYF--SKET SFQKGSPASK -----VTTMG

EGDFRHKSSF VI
ENDFRHTKSF II
```

FIG. 3

FIG. 4A

Murine and human JAM-2 (CRAM-1)

```
              10              20
moJAM-2 (CR1)  MALSRRLRRIYARLPHFIEFR
huJAM-2 (CR1)  MALRPPRELCAPDFLLLFR
               MAL R  RLRL    ARLP  FFLLLFR 30              40              50
moJAM-2 (CR1)  GCMTEAVNLKSSNRPVVHEESVE
huJAM-2 (CR1)  GCLIGAVNLKSSNRTPVVQEFESVE
               GC I AVNLKSSNR PVV EFESVE 60              70
moJAM-2 (CR1)  LSCIITHSQTSDPRIEWKIQDGQT
huJAM-2 (CR1)  LSCIIDSQTSDPRIEWKIQDEQT
               LSCIIT SQTSDPRIEWKKIQD QT 80              90             100
moJAM-2 (CR1)  TYVFDNKIQGDIAGRTDVFGKTSL
huJAM-2 (CR1)  TYVFDNKIQGDLAGRAEILGKTSL
               TYV FDNKIQGDLAGR       GKTSL
```

FIG. 4B

Murine and human JAM-2 (CRAM-1)

```
                    110              120
moJAM-2 (CR1)  R I W N V T R S D S A I Y R C E V V A L N D R K E
huJAM-2 (CR1)  K I W N V T R R D S A L Y R C E V V A R N D R K E
               . I W N V T R   D S A . Y R C E V V A   N D R K E 130              140              150
moJAM-2 (CR1)  V D E I T E L I V Q V K P V T P V C R I P A V
huJAM-2 (CR1)  I D E I I E L T V Q V K P V T P V C R V P K A V
               . D E I   E L   V Q V K P V T P V C R . P   A V 160              170
moJAM-2 (CR1)  P V G K T A T L C Q E S E G Y P R P H Y S W Y R
huJAM-2 (CR1)  P V G K M A T L H Q E S E G H P R P H Y S W Y R
               P V G K   A T L . C Q E S E G   P R P H Y S W Y R 180              190              200
moJAM-2 (CR1)  N D V P L P T D S R A N P R F Q N S S F H V N S E
huJAM-2 (CR1)  N D V P L P T D S R A N P R F R N S S F H L N S E
               N D V P L P T D S R A N P R F . N S S F H . N S E
```

FIG. 4C      Murine and human JAM-2 (CRAM-1)

```
            210                  220
moJAM-2 (CR1)  TGTLVF N AVHKDDSGQYYCIASNDA
huJAM-2 (CR1)  TGTLVF T AVHKDDSGQYYCIASNDA
               TGTLVF . AVHKDDSGQYYCIASNDA 230          240              250
moJAM-2 (CR1)  G A RCE G QD MEAVYDLNI T AG GIIGGVL
huJAM-2 (CR1)  G S RCE E QE MEVVYDLNI G G  GIIGGVL
               G . RCE   Q  ME VYDLNI       GIIGGVL 260                 270
moJAM-2 (CR1)  VVL I VLA V ITM GICCAYRRG CF I SS
huJAM-2 (CR1)  VVL A VLA L IT  GICCAYRRG  Y  NN
               VVL   VLA . IT  GICCAYRRG F I 280          290              300
moJAM-2 (CR1)  KQDGES YK S PGK H DGVNYIRT S EEG
huJAM-2 (CR1)  KQDGDS  K N PGK P DGVNYIRT D EEG
               KQDGES YK   PGK   DGVNYIRT   EEG
```

FIG. 4D  Murine and human JAM-2 (CRAM-1)

moJAM-2 (CR1)  D F R H K S S T V I
huJAM-2 (CR1)  D F R H K S S F V I

FIG. 5A  Murine and human CRAM-2 (JAM-3)

```
                              10                    20
huJAM-3(CRAM-2)
moJAM-3(CRAM-2)  M A R S P Q G L L M L L L L H Y L I V A L D Y H K 30                    40                    50
huJAM-3(CRAM-2)
moJAM-3(CRAM-2)  A N G F S A S K D H R Q E V T V I E F Q E A I L A 60                    70
huJAM-3(CRAM-2)
moJAM-3(CRAM-2)  C K T P K K T T S S R L E W K K V G Q G V S L V Y 80                    90                   100
huJAM-3(CRAM-2)                              R A E M I D F N I R I K N V
moJAM-3(CRAM-2)  Y Q Q A L Q G D F K D  R A E M I D F N I R I K N V
```

FIG. 5B  Murine and human CRAM-2 (JAM-3)

```
                        110                  120
huJAM-3(CRAM-2)   TRSDAG KYRCEVSAP A EQGNLEED
moJAM-3(CRAM-2)   TRSDAG E YRCEVSAP T EQGNLQED
                  TRSDAG   YRCEVSAP . EQGQNL.ED 130              140                150
huJAM-3(CRAM-2)   T VT LEVLVAPAVP S CEVPS      ALSGT
moJAM-3(CRAM-2)   K VM LEVLVAPAVP A CEVPT      SVMTGS
                  V    LEVLVAPAVP . CEVP . S . . G .

160                     170
huJAM-3(CRAM-2)   VVELRCQDKEGNPAPEY T WFKDGIR
moJAM-3(CRAM-2)   VVELRCQDKEGNPAPEY I WFKDGTS
                  VVELRCQDKEGNPAPEY   WFKDG 180               190              200
huJAM-3(CRAM-2)   LL ENP RLGSQ TNSSY IMNTKTGTL
moJAM-3(CRAM-2)   LE NP - KGTHN NSSY TNEHESGIL
                  LL NP          NSSYT       . G . L
```

FIG. 5C  Murine and human CRAM-2 (JAM-3)

```
                        210                    220
huJAM-3(CRAM-2)  Q F N T V S K L D T G T Y S C E A R N S V G Y R R
moJAM-3(CRAM-2)  Q T N M I S K M D S G E Y C E A R N S V G H R R
                 Q F N . S K . D . G E Y   C E A R N S V G   R R 230                    240            250
huJAM-3(CRAM-2)  C P G K R M Q V D D L N I S G I I A A V V V A L
moJAM-3(CRAM-2)  C P G K R M Q V D V L N I S G I I A T V V V A F
                 C P G K R M Q V D   L N I S G I I A . V V V A 260                    270
huJAM-3(CRAM-2)  V I S V C G L G V C Y A Q R K G Y F S K E T S F Q
moJAM-3(CRAM-2)  V T S V G G L G T G Y A Q R K G Y F S K E T S F Q
                 V I S V C G L G   C Y A Q R K G Y F S K E T S F Q 280                    290            300
huJAM-3(CRAM-2)  K S N S S K A T T M S E N D F K H T K S F I I
moJAM-3(CRAM-2)  K G S P A S K V T T M G E N D F R H T K S F I L
                 K . S   . S K . T T M   E N D F . H T K S F I
```

>Nucleic acid sequence huCRAM-1/ huJAM-2
ATGGCGCTGAGGCGGCCACCGCGACTCCGGCTCTGCGCTCGGC
TGCCTGACTTCTTCCTGCTGCTGCTTTTCAGGGGCTGCCTGAT
AGGGGCTGTAAATCTCAAATCCAGCAATCGAACCCCAGTGGTA
CAGGAATTTGAAAGTGTGGAACTGTCTTGCATCATTACGGATT
CGCAGACAAGTGACCCCAGGATCGAGTGGAAGAAAATTCAAGA
TGAACAAACCACATATGTGTTTTTGACAACAAAATTCAGGGA
GACTTGGCGGGTCGTGCAGAAATACTGGGGAAGACATCCCTGA
AGATCTGGAATGTGACACGGAGAGACTCAGCCCTTTATCGCTG
TGAGGTCGTTGCTCGAAATGACCGCAAGGAAATTGATGAGATT
GTGATCGAGTTAACTGTGCAAGTGAAGCCAGTGACCCCTGTCT
GTAGAGTGCCGAAGGCTGTACCAGTAGGCAAGATGGCAACACT
GCACTGCCAGGAGAGTGAGGGCCACCCCCGGCCTCACTACAGC
TGGTATCGCAATGATGTACCACTGCCCACGGATTCCAGAGCCA
ATCCCAGATTTCGCAATTCTTCTTTCCACTTAAACTCTGAAAC
AGGCACTTTGGTGTTCACTGCTGTTCACAAGGACGACTCTGGG
CAGTACTACTGCATTGCTTCCAATGACGCAGGCTCAGCCAGGT
GTGAGGAGCAGGAGATGGAAGTCTATGACCTGAACATTGGCGG
AATTATTGGGGGGGTTCTGGTTGTCCTTGCTGTACTGGCCCTG
ATCACGTTGGGCATCTGCTGTGCATACAGACGTGGCTACTTCA
TCAACAATAAACAGGATGGAGAAAGTTACAAGAACCCAGGGAA
ACCAGATGGAGTTAACTACATCCGCACTGACGAGGAGGGCGAC
TTCAGACACAAGTCATCGTTTGTGATCTGAGACCCGGGTGTGG
CTGAGAGCGCACAGAGCCGCACGTGCACATACCTCTGCTAGAA
ACTCCTGTCAAGGCAGCGAGAGCTGATGCACTCGACAGAGCTA
GACACTCTTCAAAGCTTTTCGTTTGGCAAGGTGACCACTACTC
TTTTACTCTACAAGCCCATGAAAAGAGAAATTTTCTCAAGAGG
ACCCGGAAATATAACCCCAAGGAACCAAACTGGGTGCGTTCAC
TGAGGTGGGGTCCTTAATTTGTTTTTGGCCTGATTCCCATGAA
AATAAGGGGTCTTTAAGAGTTTGGTACGTAAAACCCCCGCTT
GGGCCTTGGAAACCACATGTTTACCACCTGCGTTAAAAAAAAA
AAAAAA

*FIG. 6A*

>huCRAM-1/huJAM-2 complete
MALRRPPRLRLCARLPDFFLLLLFRGCLIGAVNLKSSNRTPVV
QEFESVELSCIITDSQTSDPRIEWKKIQDEQTTYVFFDNKIQG
DLAGRAEILGKTSLKIWNVTRRDSALYRCEVVARNDRKEIDEI
VIELTVQVKPVTPVCRVPKAVPVGKMATLHCQESEGHPRPHYS
WYRNDVPLPTDSRANPRFRNSSFHLNSETGTLVFTAVHKDDSG
QYYCIASNDAGSARCEEQEMEVYDLNIGGIIGGVLVVLAVLAL
ITLGICCAYRRGYFINNKQDGESYKNPGKPDGVNYIRTDEEGD
FRHKSSFVI >huCRAM-2/huJAM-3 partial
RAEMIDFNIRIKNVTRSDAGKYRCEVSAPAEQGQNLEEDTVTL
EVLVAPAVPSCEVPSSALSGTVVELRCQDKEGNPAPEYTWFKD
GIRLLENPRLGSQSTNSSYTMNTKTGTLQFNTVSKLDTGEYSC
EARNSVGYRRCPGKRMQVDDLNISGIIAAVVVALVISVCGLG
VCYAQRKGYFSKETSFQKSNSSSKATTMSENDFKHTKSFII

*FIG. 6B*

| Y | R | C | X | A | S1 |
| TAY | AGN | TGY | NNN | GCY | TCY AA |

| Y | R | C | X | A | S2 |
| TAY | AGN | TGY | NNN | GCY | AGY AA |

| Y | Q | C | X | A | S1 |
| TAY | CRG | TGY | NNN | GCY | TCY AA |

| Y | Q | C | X | A | S2 |
| TAY | CRG | TGY | NNN | GCY | AGY AA |

| Y | Y | C | X | A | S1 |
| TAY | TAY | TGY | NNN | GCY | TCY AA |

| Y | Y | C | X | A | S2 |
| TAY | TAY | TGY | NNN | GCY | AGY AA |

```
gacattcccctcgacatggcggctgctgagccgggcgctgctgcgactgctacgcgcgctg        60
                    M  A  L  S  R  R  L  R  L  L  R  L  Y  A  R  L   15
cctcacttcttcctgctgctcttcaggggctgcatgatagaggcagtgaatctcaaa          120
 P  H  F  F  L  L  L  F  R  G  C  M  I  E  A  V  N  L  K            35
tccagcaaccgaaaccagtggtacatgaatttgaagtgtggaatcttgcatcatt           180
 S  S  N  R  N  P  V  H  E  F  E  S  V  E  L  S (C) I  I            55
acgcactcacagacaagtgaccccagagattgaatggaagaaaatccaagatggccaaacc      240
 T  H  S  Q  T  S  D  P  R  I  E  W  K  K  I  Q  D  G  Q  T         75
acatatgtgtattttgacaacagattcaaggagacctgcaggtcgcacagatgtgttt         300
 T  Y  Y  F  D  N  K  I  Q  G  D  L  A  G  R  T  D  V  F            95
ggaaaacttccctgaggatctgaatgtgacacgaagcgatcagccatctatcgctgt         360
 G  K  T  S  L  R  I  W  N  V  T  R  S  D  S  A  I  Y  R  (C)      115
gaggtcgttgctctaaatgaccgaaaagaagttgatgagattaccattgattgttgtg        420
 E  V  A  L  N  D  R  K  E  V  D  E  I  T  I  E  L  I  V           135
caagtgaagccagtgacccctgcagaattccagccgctgtacctgtaggcaagacg          480
 Q  V  K  P  V  T  P  V  C  R  I  P  A  A  V  P  V  G  K  T        155
```

*FIG. 8A*

```
gcaacactgcagtgccaagagagcgagggctatccccggcctcactacagctggtaccgc 540
 A  T  L  Q (C) Q  E  S  E  G  Y  P  R  P  H  Y  S  W  Y  R   175
aatgatgtgccactgcctgcctacagattccagagccaattccagttccagaattcctttc 600
 N  D  V  P  L  P  T  D  S  R  A  N  P  R  F  Q  N  S  S  F   195
catgtgaactcggagacaggactctggtttcaatgctgtccaaggacgactctggg 660
 H  V  N  S  E  T  G  T  L  V  F  N  A  V  H  K  D  D  S  G   215
cagtactactgcattggcttccaatgacgcaggtgcagcaggtgtgaggggcaggacatg 720
 Q  Y  Y (C) I  A  S  N  D  A  G  A  A  R  C  E  G  Q  D  M   235
gaagtctatgattgaacattgctgggattattgggagtcctgttgtcctgtcctattgtt 780
 E  V  Y  D  L  N  I  A  G  I  I  G  G  V  L  V  L  L  I  V   255
cttgctgtgattacgatgggcatctgctgtgctacagacgaggctgcttcatcagcagt 840
 L  A  V  I  T  M  G  I  C  C  A  Y  R  R  G  C  F  I  S  S   275
aaacaagatggagaaagctataagagccagggaagcatgacggttaactacatcccgg 900
 K  Q  D  G  E  S  Y  K  S  P  G  K  H  D  G  V  N  Y  I  R   295
acgagtgaggagggtgactcagacaatcgtccttgtattctgacacctgtcggct 960
 T  S  E  E  G  D  F  R  H  K  S  S  F  V  I  *               310
```

*FIG. 8B*

```
gggagagcacatgcaagtagtacctctgttggaagctgtggtcacagggctgctgtgagcccaga 1020
gctcctgacaaagccacccgggcagagaagcttttgttttggccaaagttgatgactcctt 1080
ccttcctcctccttcttaacaagcctacctgacctcattatggggattagggtgatcttcaaggcc 1140
gtagacagattgtgctagcctgacctcattatggggattagggtgatcttcaaggcc 1200
tttctggtctccgttctccgtcccatgcagggcaatttgactgtgtttttgccccagctgttta 1260
gctgccaggacaacactggcagagagaggctgaggcgctgagtgagcagcaggca 1320
acagcctgatgcctgtgacagtgccccaggaagttttcaggcagtgcctgctccctgg 1380
acccctgaccaccgtgtgcctctgttgccagtactgtcattccatcctggaga 1440
atgtgtttgaatcagcatttttataaaaaccaaatcagaaaggtgaaattgcttgctg 1500
ggaagagggctctgacccaggaaactctcctcccagagatgccaggagataggagaaac 1560
ctgtctgtcttaagtctgaaatggtactgaagtctcctttctattggtcttgctcttattt 1620
tataaaaattaacattctaaatttgctagagatgtttcaaaacgtatttttataatgagttc 1680
tataaactgtaaatgtaggcttgggctgctagtgttaattggaaaataccagtagtaaagtc 1740
aacttaaggtagaaggcttcttaaggaggctgctgaatattcctttgttcaaagaagttag 1800
tttaaggagttttcttaaggaggctgctgaatattcctttgttcaaagaagttag 1860
cattttcataagaaactactctgtcctgaccactgttgcttaggaaccattaaagaa 1920
ttccaatctaaaaaaaaaa
```

*FIG. 8C*

FIG. 9A

```
                                        20                              40
CRAM-1     : MA GSRRLRLRLYARLPHFLFLLFR                GCMIEAVNLKSSNRNPVVHEFESVE
CRAM-2     : MARSPQGLLMLLLHVLIVALDY                   HKANGFSASKDHRQEVTVIEFQEAI
JAM        :    MGTECKAGRKLLFTSMILG                   SLVQGKGSVYTAQSDVQVPEMESIK
Consensus  :          r     l    Llh f  l             c  k             v  Ef  s

*                  60                              80      *
CRAM-1     : LSCITHSQTSDPRIEWKKIQDGQT                 TYVYFDNKIQGDLAGRTDVFGKTSL    : 100
CRAM-2     : LACK-TPKKTSSRIEWKKVGQG-V                 SLVYQQALQGDFKDRAEMID-FNI     : 95
JAM        : LTC--TYSGFSSPRVEWKFVQGSTT                ALVCYNSQITAPYADRV-TESSEGI    : 93
Consensus  : L  C    T  s sspR EWKK  q  e                  adR       e    i
                                        100
```

FIG. 9B

```
                              *            120
CRAM-1     : RIWNVTRSDSAIYRCEVVALNDR-K
CRAM-2     : RIKNVTRSDAGEYRCEVSAPTEQGQ
JAM        : TFSSVTRKDNGEYTCMVS--EEGGQ
Consensus  : ri nVTRsD qeYrCevsa    gq

*              *
                         140
CRAM-1     : EVDETIELIVQVKPVTPVCRIPAA
CRAM-2     : NLQEDKVMLEVLVAPAVPACEVPTS
JAM        : NYGEVSIHLTVLVPPSKPTISVPSS
Consensus  :   E    L VLVP P      Ps 160      *
CRAM-1     : VPVGKTATLQCQESEGYPRPHYSWY
CRAM-2     : VMTGSVVELRCQDKEGNPAPEYIMF
JAM        : VTIGNRAVLTCSEHDGSPPSEYSWF
Consensus  : V  G   a L C  e G P  eYsW 200
CRAM-1     : RNDVPLPT-DSRANPREQNSSFHVN : 198
CRAM-2     : KDGTSLIG-NPKGGTH-NNSSYTNE : 193
JAM        : KDGISMLTADAKKTRAEHNSSETID : 191
Consensus  : k   le      k  f  NSS g
```

FIG. 9C

```
                      220*
CRAM-1      : SETGTLVFNAVHKDDSGQYYCIASN :
CRAM-2      : HESGILQFNMISKMDSGEYYCEARN :
JAM         : PKSGDLYFDFVTAFDSGEYYCQAQN :
Consensus   :  esG  F  k   DSG YYC  A N
                       240

*
CRAM-1      : DAGAA-RCEGQDMEVYDLNIAGIIG :
CRAM-2      : SVGHR-RCPGKRMQVDVLNISGIIA :
JAM         : GYGTAMRSEAAHMDAVELNVGGIVA :
Consensus   :  G a Rceg  M V LN  GI a
                            260

CRAM-1      : GVLVLIVLAVITMGTCCAYRRGCF :
CRAM-2      : TVVVAFVISVCGIETCYAQRKGYF :
JAM         : AVLVTLILGLEIFGVWEAYSRGYF :
Consensus   :  v v iv  v      G  A  rGvF
                        280            300

CRAM-1      : ISSKQDGESYKSPGKHDGVNYERTS :  297
CRAM-2      : --SKETSFQKGSPASK----VETM :  285
JAM         : ---ETKKGTAPGKKVIYSQPSTR :  287
Consensus   :    sk t       sPgkk     T
```

FIG. 9D

```
CRAM-1     : EGDFRHKSSFVI : 310
CRAM-2     : GENDFRHTKSFII : 298
JAM        : SEGEFKQTSSFLV : 300
Consensus  : Eg  FrhtssF
```

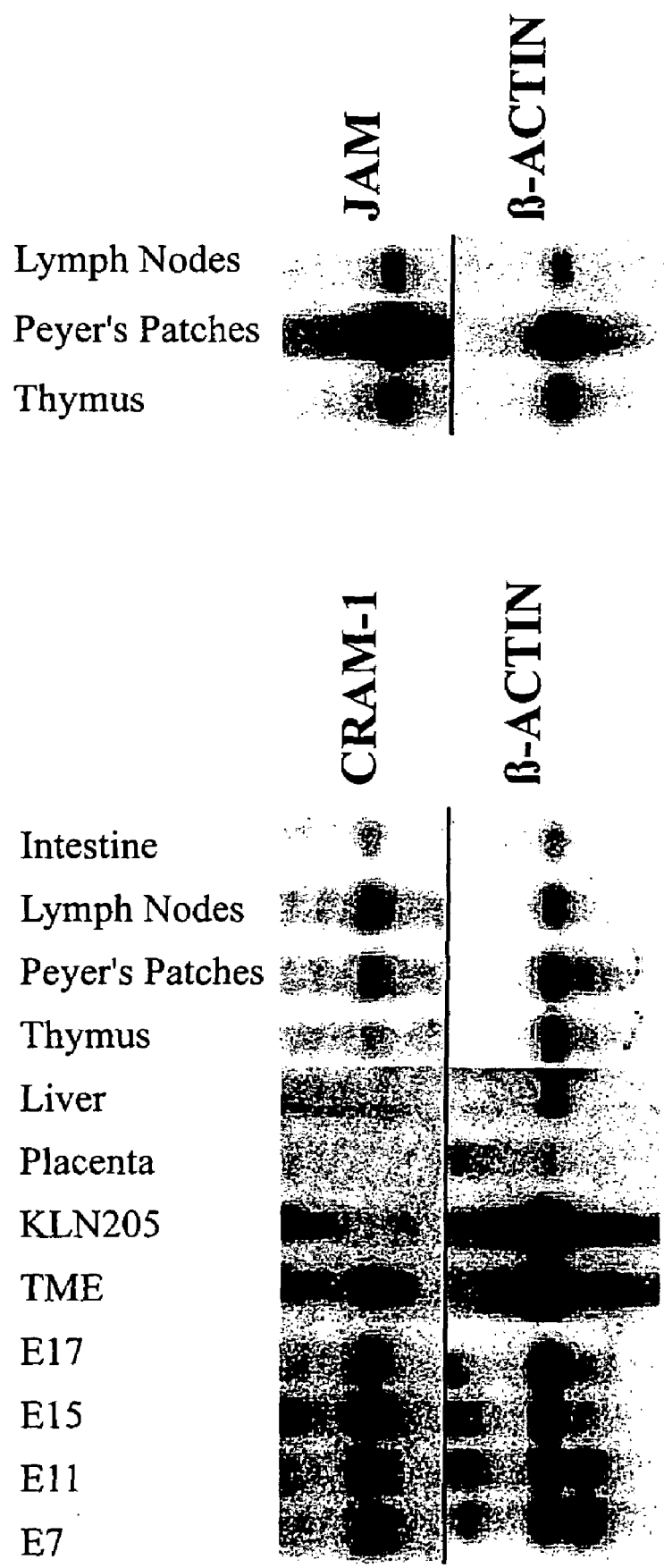

FIG. 14
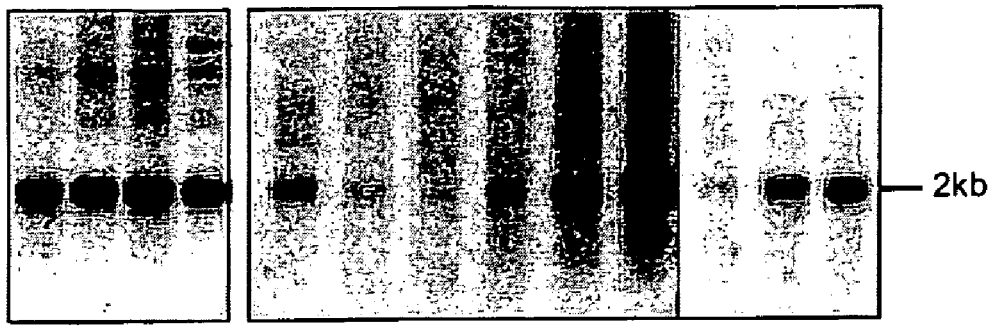
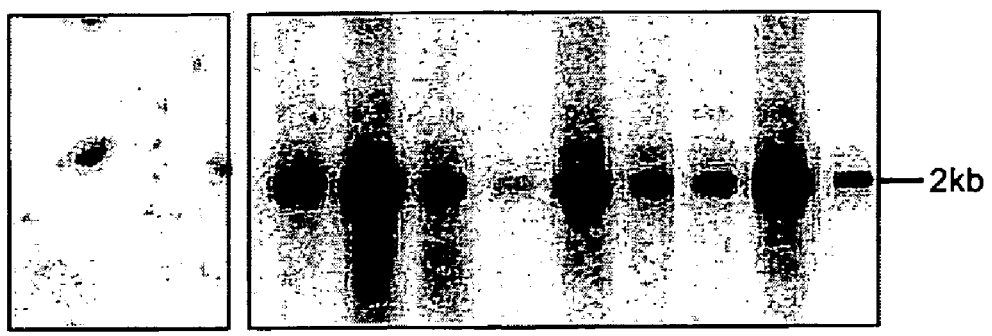
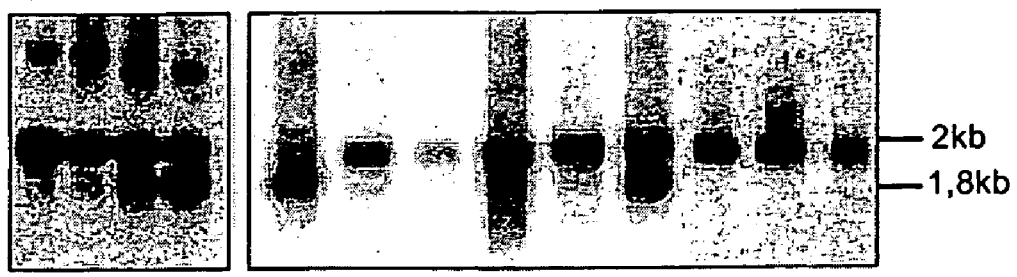

SEQUENCE LISTING

```
<160> NUMBER OF SEQ ID NOS: 31

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (6)
<223> OTHER INFORMATION: a, t, c, g, other or unknown
<220> FEATURE:
<221> NAME/KEY: modified_base
<222> LOCATION: (10)..(12)
<223> OTHER INFORMATION: a, t, c, g, other or unknown

<400> SEQUENCE: 1
tayagntgyn nngcytcyaa                                               20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (10)..(12)
<223> OTHER INFORMATION: a, t, c, g, other or unknown

<400> SEQUENCE: 2
taycrgtgyn nngcytcyaa                                               20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (10)..(12)
<223> OTHER INFORMATION: a, t, c, g, other or unknown

<400> SEQUENCE: 3
taytaytgyn nngcytcyaa                                               20

<210> SEQ ID NO 4
<211> LENGTH: 18
<212> TYPE: DNA
```

-continued

<213> ORGANISM: Artificial Sequence
<220> FEATURE:
<223> OTHER INFORMATION: Description of Artificial Sequence: primer

<400> SEQUENCE: 4
gaggtacttg catgtgct                                                    18

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 5
cgacaggtgt cagataaca                                                   19

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 6
caccctcctc actcgt                                                      16

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: primer used
      for detection of JAM-2 transcript

<400> SEQUENCE: 7
gactcacaga caagtgac                                                    18

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: primer used
      for detection JAM-2 transcript

<400> SEQUENCE: 8
caccctcctc actcgt                                                      16

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: primer for
      Hprt cDNA

<400> SEQUENCE: 9
gttggataca ggccagactt tgttg                                            25

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: primer for
      Hprt cDNA

<400> SEQUENCE: 10
gagggtaggc tggcctatag gct                                              23

<210> SEQ ID NO 11
<211> LENGTH: 1943
<212> TYPE: DNA
<213> ORGANISM: Mus musculus

<400> SEQUENCE: 11

```
cagacattcc cctcgacatg gcgctgagcc ggcggctgcg acttcgactg tacgcgcggc        60
tgcctgactt cttcctgctg ctgctcttca ggggctgcat gatagaggca gtgaatctca       120
aatccagcaa ccgaaaccca gtggtacatg aatttgaaag tgtggaattg tcttgcatca       180
ttacggactc acagacaagt gaccctagga ttgaatggaa gaaaatccaa gatggccaaa       240
ccacatatgt gtattttgac aacaagattc aaggagacct ggcaggtcgc acagatgtgt       300
ttggaaaaac ttccctgagg atctggaatg tgacacgatc ggattcagcc atctatcgct       360
gtgaggtcgt tgctctaaat gaccgaaaag aagttgatga gattaccatt gagttaattg       420
tgcaagtgaa gccagtgacc cctgtctgca gaattccagc cgctgtacct gtaggcaaga       480
cggcaacact gcagtgccaa gagagcgagg gctatccccg gcctcactac agctggtacc       540
gcaatgatgt gccactgcct acagattcca gagccaatcc caggttccag aattcctctt       600
tccatgtgaa ctcggagaca ggcactctgg ttttcaatgc tgtccacaag gacgactctg       660
ggcagtacta ctgcattgct ccaatgacg caggtgcagc caggtgtgag gggcaggaca       720
tggaagtcta tgatttgaac attgctggga ttattggggg agtccttgtt gtccttattg       780
ttcttgctgt gattacgatg ggcatctgct gtgcgtacag acgaggctgc ttcatcagca       840
gtaaacaaga tggagaaagc tataagagcc cagggaagca tgacggtgtt aactacatcc       900
ggacgagtga ggagggtgac ttcagacaca atcgtccttt gttatctga cacctgtcgg       960
ctgggagagc acatgcaagt acctctgttg gaagctggtc acagggctgc tgtgagccca      1020
gagctcctga caaagccacc cgggcagaag cttttttgttt tggccaaagt tgatgactcc      1080
ttccttcctt ccttcctctt taacaagcca caagaataaa aggaagcctc ctgaagatgg      1140
atgtagacac agattgttgc tagcctgacc tcattatggg gattagggtg atcttcaagg      1200
cctttctggt ctccgttctc ccatgcaggg caatttggac tgttttttgcc ccaggctgtt      1260
tagctgccag acaacactg gcagagagag gctgaggcgc tgggctgcag tagcagcagg       1320
caacagcctg atgcctgtga cagtgcccca ggaaggtttt caggcagtgc cttgctccct      1380
ggaccctgac ccaccgtgtt gcctctgttg attggccagt actgtcattt ccatcctgga      1440
gaatgtgttt ggaatcagca ttttataaaa aacccaaatc agaaaggtga aattgcttgc      1500
tgggaagagg gctctgaccc aggaaactct ccttcccaag agatgccagg agataggaga      1560
acctgtctgt cttaagtctg aaatggtact gaagtctcct tttctattgg tcttgcttat      1620
tttataaaaa tttaacattc taaattttgc tagagatgta ttttgattac tgaaaatttc      1680
tatataaact gtaaatatat tgccatacag tgtttcaaaa cgtatttttt tataatgagt      1740
tcaacttaag gtgaaaggct tgggctgcta gtgtttaatt ggaaaatacc agtagtaaag      1800
tcttttaagg agttttctta aggaggctgg ctgaatattc ctttgttcaa aagaagtttt      1860
agcattttc ataagaaaac ttactctgtc tgaccactgt tgcttaggaa accattaaag       1920
aattccaatc taaaaaaaaa aaa                                              1943
```

<210> SEQ ID NO 12
<211> LENGTH: 1626
<212> TYPE: DNA
<213> ORGANISM: Mus musculus

<400> SEQUENCE: 12

| | | | | | |
|---|---|---|---|---|---|
| cagaattcgg | cacgagggtc | tgggggcggg | gggccgacct | acgggttctc | cctcaagagc | 60 |
| taatctctgc | cgccactcgc | ttaggaccct | gcggacaccg | cgtcccgcgt | ccacgccctc | 120 |
| ccctcaaccc | tcttccaccc | ttcaaaagaa | ggactgtcca | gacaccacgt | cctagggcca | 180 |
| gaagacctgc | ccccacgaca | gtcgctggag | acacccagga | ccggagagac | tgacatcggg | 240 |
| acaggacccg | cccctctgct | tccacctctc | agggacctcc | tctgctccgc | cgccgggcga | 300 |
| agtgctggga | gacccagccg | cctgtcgcgc | tcctgcaggg | ggaccctcag | ctaggcagcc | 360 |
| agctggcgcc | cgcgtagatg | gcgaggagcc | cccaaggcct | cctgatgctg | ctgctgctac | 420 |
| actacttgat | cgtcgccctg | gactatcata | aggcaaatgg | gttttctgca | tcaaaagacc | 480 |
| accgtcaaga | agtcacagta | atagagttcc | aagaggctat | tttggcttgt | aaaaccccaa | 540 |
| agaagactac | ctcctccaga | ctggagtgga | agaaggtggg | acaggggtc | tccttggtct | 600 |
| actaccaaca | ggctctccaa | ggtgacttta | agaccgtgc | tgagatgata | gatttcaata | 660 |
| tacgaatcaa | aaatgttaca | agaagtgatg | ctggagagta | tcgctgtgaa | gtcagcgctc | 720 |
| cgactgagca | aggccagaac | ctgcaggaag | ataaagtcat | gctagaagta | ctagtggctc | 780 |
| ctgctgttcc | tgcctgtgaa | gtgcccactt | ctgttatgac | tggaagtgtg | gtggagctac | 840 |
| gatgccagga | taaagaagga | aacccagctc | cggagtacat | ctggtttaaa | gatggcacaa | 900 |
| gtttgctagg | gaatccaaaa | gcggcacac | acaacaacag | ctcgtacaca | aatgaacacg | 960 |
| aatctggaat | tctgcaattc | aacatgattt | ccaagatgga | cagtggagag | tattactgcg | 1020 |
| aagcccggaa | ctctgtcgga | caccgcaggt | gccctgggaa | gcgaatgcaa | gtagatgttc | 1080 |
| tcaacataag | cggcatcata | gcaacggttg | tggtggtggc | cttcgtgatt | tctgtatgtg | 1140 |
| gccttggcac | atgctatgct | cagaggaaag | gctactttc | aaaagaaact | tccttccaga | 1200 |
| agggcagtcc | tgcatctaaa | gtcactacga | tgggcgaaaa | tgatttcagg | cacacaaaat | 1260 |
| cctttataat | ttaaaagaat | tccagttttg | ggctgcccaa | aaccagttgt | cacatgttat | 1320 |
| taaaatattg | taaaactctg | tgtcttacac | ttgcaaagtg | atgaagaaat | atgaaagggg | 1380 |
| agttcatcag | aagttttatg | atctctaact | cacaagaaat | attttaagca | aaacgttctt | 1440 |
| gccatcacta | aattacaacc | tggcatcttg | tgttgaccta | aggaaatgt | ctggtaatat | 1500 |
| tctggttttt | gaaggcaaat | gaatgtcagt | ttggagttga | ctatatcaca | ctgactgtaa | 1560 |
| ggctaatcca | agaagcaaga | atataaaaaa | aaaaaaaaa | aaaaaaaaa | aaaaaaaaa | 1620 |
| aatttc | | | | | | 1626 |

<210> SEQ ID NO 13
<211> LENGTH: 310
<212> TYPE: PRT
<213> ORGANISM: Mus musculus

<400> SEQUENCE: 13

Met Ala Leu Ser Arg Arg Leu Arg Leu Arg Leu Tyr Ala Arg Leu Pro
1               5                   10                  15

His Phe Phe Leu Leu Leu Leu Phe Arg Gly Cys Met Ile Glu Ala Val
            20                  25                  30

Asn Leu Lys Ser Ser Asn Arg Asn Pro Val Val His Glu Phe Glu Ser

-continued

```
                35                  40                  45
Val Glu Leu Ser Cys Ile Ile Thr His Ser Gln Thr Ser Asp Pro Arg
 50                  55                  60

Ile Glu Trp Lys Lys Ile Gln Asp Gly Gln Thr Thr Tyr Val Tyr Phe
 65                  70                  75                  80

Asp Asn Lys Ile Gln Gly Asp Leu Ala Gly Arg Thr Asp Val Phe Gly
                 85                  90                  95

Lys Thr Ser Leu Arg Ile Trp Asn Val Thr Arg Ser Asp Ser Ala Ile
                100                 105                 110

Tyr Arg Cys Glu Val Val Ala Leu Asn Asp Arg Lys Glu Val Asp Glu
                115                 120                 125

Ile Thr Ile Glu Leu Ile Val Gln Val Lys Pro Val Thr Pro Val Cys
130                 135                 140

Arg Ile Pro Ala Ala Val Pro Val Gly Lys Thr Ala Thr Leu Gln Cys
145                 150                 155                 160

Gln Glu Ser Glu Gly Tyr Pro Arg Pro His Tyr Ser Trp Tyr Arg Asn
                165                 170                 175

Asp Val Pro Leu Pro Thr Asp Ser Arg Ala Asn Pro Arg Phe Gln Asn
                180                 185                 190

Ser Ser Phe His Val Asn Ser Glu Thr Gly Thr Leu Val Phe Asn Ala
                195                 200                 205

Val His Lys Asp Asp Ser Gly Gln Tyr Tyr Cys Ile Ala Ser Asn Asp
                210                 215                 220

Ala Gly Ala Ala Arg Cys Glu Gly Gln Asp Met Glu Val Tyr Asp Leu
225                 230                 235                 240

Asn Ile Ala Gly Ile Ile Gly Gly Val Leu Val Val Leu Ile Val Leu
                245                 250                 255

Ala Val Ile Thr Met Gly Ile Cys Cys Ala Tyr Arg Arg Gly Cys Phe
                260                 265                 270

Ile Ser Ser Lys Gln Asp Gly Glu Ser Tyr Lys Ser Pro Gly Lys His
                275                 280                 285

Asp Gly Val Asn Tyr Ile Arg Thr Ser Glu Glu Gly Asp Phe Arg His
                290                 295                 300

Lys Ser Ser Phe Val Ile
305                 310

<210> SEQ ID NO 14
<211> LENGTH: 298
<212> TYPE: PRT
<213> ORGANISM: Mus musculus

<400> SEQUENCE: 14

Met Ala Arg Ser Pro Gln Gly Leu Leu Met Leu Leu Leu Leu His Tyr
  1               5                  10                  15

Leu Ile Val Ala Leu Asp Tyr His Lys Ala Asn Gly Phe Ser Ala Ser
                 20                  25                  30

Lys Asp His Arg Gln Glu Val Thr Val Ile Glu Phe Gln Glu Ala Ile
                 35                  40                  45

Leu Ala Cys Lys Thr Pro Lys Lys Thr Thr Ser Ser Arg Leu Glu Trp
 50                  55                  60

Lys Lys Val Gly Gln Gly Val Ser Leu Val Tyr Tyr Gln Gln Ala Leu
 65                  70                  75                  80

Gln Gly Asp Phe Lys Asp Arg Ala Glu Met Ile Asp Phe Asn Ile Arg
                 85                  90                  95
```

-continued

Ile Lys Asn Val Thr Arg Ser Asp Ala Gly Glu Tyr Arg Cys Glu Val
            100                 105                 110

Ser Ala Pro Thr Glu Gln Gly Gln Asn Leu Gln Glu Asp Lys Val Met
        115                 120                 125

Leu Glu Val Leu Val Ala Pro Ala Val Pro Ala Cys Glu Val Pro Thr
    130                 135                 140

Ser Val Met Thr Gly Ser Val Val Glu Leu Arg Cys Gln Asp Lys Glu
145                 150                 155                 160

Gly Asn Pro Ala Pro Glu Tyr Ile Trp Phe Lys Asp Gly Thr Ser Leu
                165                 170                 175

Leu Gly Asn Pro Lys Gly Gly Thr His Asn Asn Ser Ser Tyr Thr Asn
            180                 185                 190

Glu His Glu Ser Gly Ile Leu Gln Phe Asn Met Ile Ser Lys Met Asp
        195                 200                 205

Ser Gly Glu Tyr Tyr Cys Glu Ala Arg Asn Ser Val Gly His Arg Arg
    210                 215                 220

Cys Pro Gly Lys Arg Met Gln Val Asp Val Leu Asn Ile Ser Gly Ile
225                 230                 235                 240

Ile Ala Thr Val Val Val Ala Phe Val Ile Ser Val Cys Gly Leu
                245                 250                 255

Gly Thr Cys Tyr Ala Gln Arg Lys Gly Tyr Phe Ser Lys Glu Thr Ser
            260                 265                 270

Phe Gln Lys Gly Ser Pro Ala Ser Lys Val Thr Thr Met Gly Glu Asn
        275                 280                 285

Asp Phe Arg His Thr Lys Ser Phe Ile Ile
    290                 295

<210> SEQ ID NO 15
<211> LENGTH: 310
<212> TYPE: PRT
<213> ORGANISM: Homo sapiens

<400> SEQUENCE: 15

Met Ala Leu Arg Arg Pro Pro Arg Leu Arg Leu Cys Ala Arg Leu Pro
1               5                   10                  15

Asp Phe Phe Leu Leu Leu Leu Phe Arg Gly Cys Leu Ile Gly Ala Val
                20                  25                  30

Asn Leu Lys Ser Ser Asn Arg Thr Pro Val Val Gln Glu Phe Glu Ser
            35                  40                  45

Val Glu Leu Ser Cys Ile Ile Thr Asp Ser Gln Thr Ser Asp Pro Arg
        50                  55                  60

Ile Glu Trp Lys Lys Ile Gln Asp Glu Gln Thr Thr Tyr Val Phe Phe
65                  70                  75                  80

Asp Asn Lys Ile Gln Gly Asp Leu Ala Gly Arg Ala Glu Ile Leu Gly
                85                  90                  95

Lys Thr Ser Leu Lys Ile Trp Asn Val Thr Arg Arg Asp Ser Ala Leu
            100                 105                 110

Tyr Arg Cys Glu Val Val Ala Arg Asn Asp Arg Lys Glu Ile Asp Glu
        115                 120                 125

Ile Val Ile Glu Leu Thr Val Gln Val Lys Pro Val Thr Pro Val Cys
    130                 135                 140

Arg Val Pro Lys Ala Val Pro Val Gly Lys Met Ala Thr Leu His Cys
145                 150                 155                 160

Gln Glu Ser Glu Gly His Pro Arg Pro His Tyr Ser Trp Tyr Arg Asn
                165                 170                 175

Asp Val Pro Leu Pro Thr Asp Ser Arg Ala Asn Pro Arg Phe Arg Asn
            180                 185                 190

Ser Ser Phe His Leu Asn Ser Glu Thr Gly Thr Leu Val Phe Thr Ala
        195                 200                 205

Val His Lys Asp Asp Ser Gly Gln Tyr Tyr Cys Ile Ala Ser Asn Asp
    210                 215                 220

Ala Gly Ser Ala Arg Cys Glu Glu Gln Glu Met Glu Val Tyr Asp Leu
225                 230                 235                 240

Asn Ile Gly Gly Ile Ile Gly Gly Val Leu Val Leu Ala Val Leu
                245                 250                 255

Ala Leu Ile Thr Leu Gly Ile Cys Cys Ala Tyr Arg Arg Gly Tyr Phe
            260                 265                 270

Ile Asn Asn Lys Gln Asp Gly Glu Ser Tyr Lys Asn Pro Gly Lys Pro
                275                 280                 285

Asp Gly Val Asn Tyr Ile Arg Thr Asp Glu Glu Gly Asp Phe Arg His
            290                 295                 300

Lys Ser Ser Phe Val Ile
305             310

<210> SEQ ID NO 16
<211> LENGTH: 212
<212> TYPE: PRT
<213> ORGANISM: Homo sapiens

<400> SEQUENCE: 16

Arg Ala Glu Met Ile Asp Phe Asn Ile Arg Ile Lys Asn Val Thr Arg
  1               5                  10                  15

Ser Asp Ala Gly Lys Tyr Arg Cys Glu Val Ser Ala Pro Ala Glu Gln
                20                  25                  30

Gly Gln Asn Leu Glu Asp Thr Val Thr Leu Glu Val Leu Val Ala Pro
            35                  40                  45

Ala Val Pro Ser Cys Glu Val Pro Ser Ser Ala Leu Ser Gly Thr Val
        50                  55                  60

Val Glu Leu Arg Cys Gln Asp Lys Glu Gly Asn Pro Ala Pro Glu Tyr
 65                  70                  75                  80

Thr Trp Phe Lys Asp Gly Ile Arg Leu Leu Glu Asn Pro Arg Leu Gly
                85                  90                  95

Ser Gln Ser Thr Asn Ser Ser Tyr Thr Met Asn Thr Lys Thr Gly Thr
            100                 105                 110

Leu Gln Phe Asn Thr Val Ser Lys Leu Asp Thr Gly Glu Tyr Ser Cys
        115                 120                 125

Glu Ala Arg Asn Ser Val Gly Tyr Arg Arg Cys Pro Gly Lys Arg Met
    130                 135                 140

Gln Val Asp Asp Leu Asn Ile Ser Gly Ile Ile Ala Ala Val Val Val
145                 150                 155                 160

Val Ala Leu Val Ile Ser Val Cys Gly Leu Gly Val Cys Tyr Ala Gln
                165                 170                 175

Arg Lys Gly Tyr Phe Ser Lys Glu Thr Ser Phe Gln Lys Ser Asn Ser
            180                 185                 190

Ser Ser Lys Ala Thr Thr Met Ser Glu Asn Asp Phe Lys His Thr Lys
        195                 200                 205

Ser Phe Ile Ile
    210

<210> SEQ ID NO 17
<211> LENGTH: 1296
<212> TYPE: DNA
<213> ORGANISM: Homo sapiens

<400> SEQUENCE: 17

| | | | | | |
|---|---|---|---|---|---|
| atggcgctga | ggcggccacc | gcgactccgg | ctctgcgctc | ggctgcctga | cttcttcctg | 60 |
| ctgctgcttt | cagggggctg | cctgataggg | gctgtaaatc | tcaaatccag | caatcgaacc | 120 |
| ccagtggtac | aggaatttga | agtgtggaa | ctgtcttgca | tcattacgga | ttcgcagaca | 180 |
| agtgacccca | ggatcgagtg | gaagaaaatt | caagatgaac | aaaccacata | tgtgtttttt | 240 |
| gacaacaaaa | ttcagggaga | cttggcgggt | cgtgcagaaa | tactggggaa | gacatccctg | 300 |
| aagatctgga | atgtgacacg | gagagactca | gcccttatc | gctgtgaggt | cgttgctcga | 360 |
| aatgaccgca | aggaaattga | tgagattgtg | atcgagttaa | ctgtgcaagt | gaagccagtg | 420 |
| accccctgtct | gtagagtgcc | gaaggctgta | ccagtaggca | agatggcaac | actgcactgc | 480 |
| caggagagtg | agggccaccc | ccggcctcac | tacagctggt | atcgcaatga | tgtaccactg | 540 |
| cccacggatt | ccagagccaa | tcccagattt | cgcaattctt | ctttccactt | aaactctgaa | 600 |
| acaggcactt | tggtgttcac | tgctgttcac | aaggacgact | ctgggcagta | ctactgcatt | 660 |
| gcttccaatg | acgcaggctc | agccaggtgt | gaggagcagg | agatggaagt | ctatgacctg | 720 |
| aacattggcg | gaattattgg | ggggggttctg | gttgtccttg | ctgtactggc | cctgatcacg | 780 |
| ttgggcatct | gctgtgcata | cagacgtggc | tacttcatca | acaataaaca | ggatggagaa | 840 |
| agttacaaga | acccagggaa | accagatgga | gttaactaca | tccgcactga | cgaggagggc | 900 |
| gacttcagac | acaagtcatc | gtttgtgatc | tgagacccgg | gtgtggctga | gagcgcacag | 960 |
| agccgcacgt | gcacataccct | tgctagaaa | ctcctgtcaa | ggcagcgaga | gctgatgcac | 1020 |
| tcgacagagc | tagacactct | tcaaagcttt | tcgtttggca | aggtgaccac | tactcttta | 1080 |
| ctctacaagc | ccatgaaaag | agaaatttc | tcaagaggac | ccggaaatat | aaccccaagg | 1140 |
| aaccaaactg | ggtgcgttca | ctgaggtggg | gtccttaatt | tgtttttggc | ctgattccca | 1200 |
| tgaaaataag | gggtctttaa | gagtttggta | cgtaaaaccc | cccgcttggg | ccttggaaac | 1260 |
| cacatgttta | ccacctgcgt | taaaaaaaaaa | aaaaaa | | | 1296 |

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: sequence
      surrounding C-terminal cysteine of C2 domain
      (endothelial cell line t-end)
<220> FEATURE:
<221> NAME/KEY: MOD_RES
<222> LOCATION: (4)
<223> OTHER INFORMATION: Any amino acid

<400> SEQUENCE: 18

Tyr

```
<220> FEATURE:
<221> NAME/KEY: MOD_RES
<222> LOCATION: (4)
<223> OTHER INFORMATION: Any amino acid

<400> SEQUENCE: 19

Tyr Gln Cys Xaa Ala Ser
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: sequence
      surrounding the C-terminal cysteine of C2 domain
      (endothelial cell line t-end)
<220> FEATURE:
<221> NAME/KEY: MOD_RES
<222> LOCATION: (4)
<223> OTHER INFORMATION: Any amino acid

<400> SEQUENCE: 20

Tyr Tyr Cys Xaa Ala Ser
1               5

<210> SEQ ID NO 21
<211> LENGTH: 300
<212> TYPE: PRT
<213> ORGANISM: Mus musculus

<400> SEQUENCE: 21

Met Gly Thr Glu Gly Lys Ala Gly Arg Lys Leu Leu Phe Leu Phe Thr
1               5                   10                  15

Ser Met Ile Leu Gly Ser Leu Val Gln Gly Lys Gly Ser Val Tyr Thr
            20                  25                  30

Ala Gln Ser Asp Val Gln Val Pro Glu Met Glu Ser Ile Lys Leu Thr
        35                  40                  45

Cys Thr Tyr Ser Gly Phe Ser Ser Pro Arg Val Glu Trp Lys Phe Val
    50                  55                  60

Gln Gly Ser Thr Thr Ala Leu Val Cys Tyr Asn Ser Gln Ile Thr Ala
65                  70                  75                  80

Pro Tyr Ala Asp Arg Val Thr Phe Ser Ser Gly Ile Thr Phe Ser
                85                  90                  95

Ser Val Thr Arg Lys Asp Asn Gly Glu Tyr Thr Cys Met Val Ser Glu
                100                 105                 110

Glu Gly Gly Gln Asn Tyr Gly Glu Val Ser Ile His Leu Thr Val Leu
            115                 120                 125

Val Pro Pro Ser Lys Pro Thr Ile Ser Val Pro Ser Ser Val Thr Ile
        130                 135                 140

Gly Asn Arg Ala Val Leu Thr Cys Ser Glu His Asp Gly Ser Pro Pro
145                 150                 155                 160

Ser Glu Tyr Ser Trp Phe Lys Asp Gly Ile Ser Met Leu Thr Ala Asp
                165                 170                 175

Ala Lys Lys Thr Arg Ala Phe His Asn Ser Ser Phe Thr Ile Asp Pro
            180                 185                 190

Lys Ser Gly Asp Leu Tyr Phe Asp Phe Val Thr Ala Phe Asp Ser Gly
        195                 200                 205

Glu Tyr Tyr Cys Gln Ala Gln Asn Gly Tyr Gly Thr Ala Met Arg Ser
    210                 215                 220
```

-continued

```
Glu Ala Ala His Met Asp Ala Val Glu Leu Asn Val Gly Gly Ile Val
225                 230                 235                 240

Ala Ala Val Leu Val Thr Leu Ile Leu Leu Gly Leu Leu Ile Phe Gly
                245                 250                 255

Val Trp Phe Ala Tyr Ser Arg Gly Tyr Phe Glu Thr Thr Lys Lys Gly
            260                 265                 270

Thr Ala Pro Gly Lys Lys Val Ile Tyr Ser Gln Pro Ser Thr Arg Ser
        275                 280                 285

Glu Gly Glu Phe Lys Gln Thr Ser Ser Phe Leu Val
    290                 295                 300

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: sequence
      surrounding the C-terminal cysteine of C2 domain
      (endothelial cell line t-end)
<220> FEATURE:
<221> NAME/KEY: MOD_RES
<222> LOCATION: (2)
<223> OTHER INFORMATION: Arg, Gln, Tyr, Ser
<220> FEATURE:
<221> NAME/KEY: MOD_RES
<222> LOCATION: (4)
<223> OTHER INFORMATION: Any amino acid
<220> FEATURE:
<221> NAME/KEY: MOD_RES
<222> LOCATION: (8)
<223> OTHER INFORMATION: Any amino acid

<400> SEQUENCE: 22

Tyr Xaa Cys Xaa Ala Ser Asn Xaa Gly
  1               5

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (6)
<223> OTHER INFORMATION: a, t, c, g, other or unknown
<220> FEATURE:
<221> NAME/KEY: modified_base
<222> LOCATION: (10)..(12)
<223> OTHER INFORMATION: a, t, c, g, other or unknown

<400> SEQUENCE: 23
tayagntgyn nngcyagyaa                                                20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (10)..(12)
<223> OTHER INFORMATION: a, t, c, g, other or unknown

<400> SEQUENCE: 24
taycrgtgyn nngcyagyaa                                                20
```

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: modified_base
<222> LOCATION: (10)..(12)
<223> OTHER INFORMATION: a, t, c, g, other or unknown

<400> SEQUENCE: 25
taytaytgyn nngcyagyaa                                            20

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: membrane
      proximal
      cytoplasmic sequence
<220> FEATURE:
<221> NAME/KEY: MOD_RES
<222> LOCATION: (2)
<223> OTHER INFORMATION: Tyr, Gln
<220> FEATURE:
<221> NAME/KEY: MOD_RES
<222> LOCATION: (3)
<223> OTHER INFORMATION: Arg, Ser
<220> FEATURE:
<221> NAME/KEY: MOD_RES
<222> LOCATION: (4)
<223> OTHER INFORMATION: Arg, Lys
<220> FEATURE:
<221> NAME/KEY: MOD_RES
<222> LOCATION: (6)
<223> OTHER INFORMATION: Cys, Tyr

<400> SEQUENCE: 26

Ala Xaa Xaa Xaa Gly Xaa Phe
 1               5

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: CK2 motif

<400> SEQUENCE: 27

Ser Lys Gln Asp
 1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: CK2 motif

<400> SEQUENCE: 28

Thr Ser Glu Glu
 1

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Tyrosine -continued

```
        kinase
        phosphorylation signature

<400> SEQUENCE: 29

Lys Gln Asp Gly Glu Ser Tyr
 1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Tyrosine
        kinase
        phosphorylation signature

<400> SEQUENCE: 30

Lys His Asp Gly val Asn Tyr
 1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: sequence
        surrounding the C-terminal cysteine of C2 domain
        (endothelial cell line t-end)
<220> FEATURE:
<221> NAME/KEY: MOD_RES
<222> LOCATION: (2)
<223> OTHER INFORMATION: Tyr, Gln, Arg
<220> FEATURE:
<221> NAME/KEY: MOD_RES
<222> LOCATION: (4)
<223> OTHER INFORMATION: Any amino acid

<400> SEQUENCE: 31

Tyr Xaa Cys Xaa Ala Ser
 1               5
```

CONFLUENCE REGULATED ADHESION MOLECULES USEFUL IN MODULATING VASCULAR PERMEABILITY

CROSS-REFERENCE TO RELATED APPLICATION

This application is a continuation of U.S. application Ser. No. 09/524,531, filed Mar. 13, 2000 now abandoned.

The present invention relates to the identification of a new subfamily of vascular adhesion molecules and to the modulation of the function of these molecules for the treatment of various diseases.

Throughout embryonic and early postnatal development, endothelial cells proliferate and differentiate to form new blood vessels via vasculogenesis and angiogenesis. In adult organisms the endothelium defines the blood-tissue barrier and consists of non-cycling quiescent cells. These polarized cells are linked to each other by tight junctions and adherens junctions to form a continuous layer of cells. The functions of the endothelial layer consist in the maintenance of tissue homeostasis, fibrinolysis, coagulation, vasotonus, and leukocyte transmigration. All these properties are controlled by a fine tuning of the expression and the function of adhesion molecules.

Pathological situations such as inflammation, tumor growth, wounding or angiogenesis lead to a temporary change of the number and function of adhesion molecules on the vascular endothelium and this results in altered homeostasis of the vessel. As an example, tumors increase the local concentration of angiogenic factors which induces a switch from non-cycling quiescent endothelial cells to proliferating endothelium. The angiogenic switch is induced by several factors including IL-8, epidermal growth factor (EGF), vascular endothelial growth factor (VEGF), soluble VCAM-1, basic fibroblast growth factor (bFGF), and tumor necrosis factor (TNF). As a result, endolhelial cells of existing vessels degrade the extracellular matrix (ECM) and invade the surrounding tissue, which leads to vascularization of tumors.

During the angiogenic switch the pattern of endothelial gene expression is modified. For example, treatment of endothelial cells with bPGF or TNFα results in a fourfold increase in $\alpha_v\beta_3$ integrin expression, an adhesion molecule implicated in endothelial cell migration. In addition, the angiogenic switch modifies the inflammatory response of endothelium leading to an abnormal migration of leukocytes toward the tumors. Normally, leukocytes extravasate from the blood by adhering to and migrating through endothelium. These mechanisms occur in a multistep process that involves selectins, integrins and Immunoglobulin Superfamily adhesion molecules.

In tumor associated endothelium VCAM, ICAM, and selectins have been shown to be downregulated. The downregulation of these adhesion molecules may represent a mechanism by which tumors avoid invasion by cytotoxic cells of the immune system.

It is the object of the present invention to search for new adhesion proteins of the Immunoglobulin Superfamily (Ig Sf), which are transcriptionally regulated in endothelium under the influence of tumors.

It is a further object of the invention to define molecules derived from the new adhesion proteins for use in the treatment of various indications, such as for example tumors and inflammation.

In the research that led to the present invention an experimental murine model was used for the identification of transcripts regulated during the co-culture of an endothelial cell line with melanoma cells. To restrict the screening strategy to adhesion molecules of the Ig Sf, a new approach of RNA display termed "Targeted Differential Display" was developed. The novelty of the modified display technique resides in the use of only one set of degenerated primers. As will be demonstrated in the examples, it was surprisingly found that this leads to sufficient specificity.

More specifically, partially degenerated primers (in the present case the level of degeneracy is between 2048 and 4096 different forms of primers within one set), designed to target the conserved sequences found in the C2 domains of Ig Sf members were used to drive the Polymerase Chain Reaction (PCR) based Targeted Differential Display technique (Samaridis & Colonna (1997) Eur. J. Immunol. 27, 660-665).

Based on this finding the invention provides a method for the specific identification of differentially expressed DNA-sequences comprising the use of Differential Display Reverse Transcription PCR, in which one set of partially or completely degenerated primers specific for the target gene is used. One major limitation of the conventional RNA display strategy is the lack of specificity of the method. In the aim to increase this specificity, the inventors in their search for other adhesion molecules used degenerated primers targeting the sequences encoding molecules with $C_2$ domains. This was achieved by the alignment of $C_2$ domains of several Ig Sf adhesion molecules, and the identification of a linear amino-acid consensus, surrounding the cysteine residue participating to the $C_2$ domain structure: Y-(RQYS)-C-x-A-S—N—$x_2$-G (SEQ ID NO:22). In a more general sense, this approach can also be used in the search for other sequences in which the reverse translation of one or more of the most frequent consensus sequences is used to design the degenerated primers used for differential display.

This method allowed the identification of a transcript, downregulated in endothelial cells by confluency in the presence of melanoma or carcinoma cells. The cDNA coded for a new molecule of the Ig Sf with the usual structural features, and was named CRAM-1 for "Confluency Regulated Adhesion Molecule". The recent description of a structurally related molecule, JAM, implicated in leukocyte transmigration, suggested the existence of a new family of adhesion molecules in which JAM and CRAM-1 were the prototypes. Sequence comparison with EST databases furthermore allowed the cloning of CRAM-2, a third member of this molecular family. FIG. 1 shows the murine cDNA sequences encoding CRAM-1 (SEQ ID NO:11) and CRAM-2 (SEQ ID NO:12) proteins. In this application the names JAM and JAM-1, CRAM-1 and JAM-2 as well as CRAM-2 and JAM-3 are used interchangeably.

The comparative tissue distribution of the transcripts encoding JAM, CRAM-1 and CRAM-2 showed a preferential expression of these molecules in endothelial and epithelial compartments suggesting a role in the maintenance of cell-cell contacts. These cell-cell interactions of quiescent endothelial cells regulate the vascular permeability, the cell cycle, and the leukocyte transmigration across endothelial wall.

To further elucidate the function and the interplay of the three molecules, a molecular approach was used. To this end, chimeric molecules were constructed consisting of Flag-tag and Enhanced Green Fluorescent Protein (EGFP) sequences fused to a soluble or a membrane bound form of CRAM-1, CRAM-2 or JAM (summarized in FIG. 2). When transfected into cell lines, the EGFP fusion products of CRAM-1 and JAM localized in cell-cell contacts, confirming a role of these molecules in the cell-cell communication. In contrast, CRAM-2 was more widely distributed on the cell surface. Moreover, the soluble construct of CRAM-1 blocked transendothelial migration of leukocytes in vitro, whereas soluble JAM showed only marginal effect. Altogether, these results suggested a central role of this new subfamily of adhesion molecules in the maintenance of vascular integrity and the function of the endothelial layer.

Based on these findings the present invention provides for new means of counteracting medical indications like chronic inflammation and tumor development with reagents based on CRAM polypeptides.

More in particular, the present invention relates to a polypeptide in isolated form belonging to a subfamily of the human Immunoglobulin Superfamily, which polypeptide shows at least 70% sequence homology with the amino acid sequence of the murine Confluency Regulated Adhesion Molecules 1 or 2 (CRAM-1 or CRAM-2) as depicted in FIG. 3 upper (SEQ ID NO:13) and second row (SEQ ID NO:14), respectively. FIGS. 4 and 5 show the alignment on amino acid level between mouse (SEQ ID NO:13; top row) and human (SEQ ID NO:15) JAM-2 (CRAM-1) and mouse (SEQ ID NO:14) and human (SEQ ID NO:16) JAM-3 (CRAM-2), respectively.

The CRAM polypeptides found in the human or animal body are markers for growing cells. CRAM expression is upregulated in cells that are growing.

Disclosed herein are two new murine polypeptides that are member of this family. Based on the sequence information of these polypeptides other members of the family can be identified by well known means such as PCR, crosshybridization on DNA libraries, crossreactivity of antibodies.

The sequence information can be either the amino acid sequence or the nucleotide sequence encoding the amino acid sequence.

More in particular, the invention thus relates to a corresponding polypeptide in humans, comprising essentially the amino acid sequence as depicted in FIG. 6B (top sequence. SEQ ID NO: 15: bottom sequence. SEQ ID NO: 16) or an amino acid sequence that is at least 70% homologous thereto.

In addition to using the sequence information of the two CRAM proteins disclosed herein for identifying other members of the family in other species,like humans, the two proteins and their corresponding family members can also be used for the preparation of derived molecules, such as antibodies directed against the (poly)peptides of the invention, or recombinant equivalents of the proteins, optionally in soluble form, or peptides comprising at least part of the amino acid sequence of the polypeptides. Suitable parts of the amino acid sequence are especially the extracellular domains: VC2, and the membrane proximal cytoplasmic sequence: A-[Y,Q]-[R,S]-[R,K]-G- [C,Y]-F (SEQ ID NO :26).

In addition to antibodies and (poly)peptide type derivatives, the invention also relates to poly- or oligonucleotides having a sequence that encodes a complete polypeptide or part thereof, which polypeptide has an amino acid sequence that is at least 70% homologous to the amino acid sequence of the CRAM-1 or CRAM-2 proteins as disclosed herein. More in particular, the invention relates to nucleotide sequences that are at least 70%, preferably at least 80%, more preferably at least 90%, most preferably essentially 100% homologous to the human DNA CRAM-1 sequence as depicted in FIG. 6A (SEQ ID NO: 17).

Such poly- or oligonucleotides may for example be RNA or DNA and can be primers, probes, antisense RNA etc.

All such molecules can be used for modulating the function of the original polypeptides found in the human or animal body or for diagnosis.

Angiogenesis in for example tumors can be inhibited with antibodies. They can be used as targeting molecules for cells bearing the CRAM polypeptides. The antibodies can act on their own or can be coupled to other molecules, such as toxins, radioactive labels, fluorescent labels, enzymatic labels, photo-activatable labels, but also to liposomes, cells, etc.

The labeled antibodies are particularly suitable for the diagnostic use of the antibodies, i.e. they can be utilized to locate angiogenesis in a growing tumor. In addition, antibodies coupled to toxins or radioactive molecules can be used to specifically kill the tumor from within by targeting to the (growing) vessels in the tumor.

It was found that CRAM-type molecules were not detected in the normal vasculature except for lymphatics and the high endothelial venules in lymphoid organs such as lymph nodes and Peyer's patches. The advantage thereof is that the targeting of for example anti-CRAM antibodies can be highly specific to for example tumor cells thus avoiding undesirable side-effects.

Moreover, the (poly)peptides may also bind the molecule on angiogenic vessels and by that stimulate or inhibit angiogenesis.

Soluble (poly)peptide having essentially the same amino acid sequence as the CRAM polypeptides can be used in the treatment of inflammation reactions of the vascular endothelium. It was found according to the invention that the transendothelial migration of leukocytes can be inhibited by sCRAM-1-IG2Do or monoclonal antibodies against CRAM-1. This and similar molecules can therefore be used to quench or stimulate an immunological reaction such as found in inflammation.

The specific expression of the molecule on vascular cells of HEVs in vivo which are specialized in lymphocyte migration argues for a stimulating effect of CRAM on lymphocyte migration or vascular permeability. This effect can thereof be due to the modulation of molecules normally involved in the sealing of the vascular bed (CRAM-1, CRAM-2, JAM, PECAM, VE-Cadherin) This finding is the basis for other applications of the invention involving the regulation of interendothelial junctions by delivering recombinant CRAM molecules (poly)peptides of the invention, or monoclonal antibodies against CRAM-1.

Anti-CRAM antibodies can also be used to block cell-cell interactions in growing cells. This leads to disorganization of intercellular contacts which are normally required for the barrier function of blood vessels. This finding may be used to increase the permeability of growing vessels to increase the delivery of drugs to sites, such as growing tumors, postmenstrual uterus, etc. The disorganization of intercellular contacts may therefore be used to block the development of tumor cells bearing the antigen, such as angiomas (tumors originating from vascular endothelium) or some rapidly growing carcinomas.

For diagnosis use can be made of labeled antibodies but also of labeled oligonucleotides that are complementary to the CRAM DNA or mRNA found in the endothelial cells expressing the CRAM protein(s).

The present invention will be further illustrated in the following example in which reference is made to the accompanying drawing, which show:

FIG. 1: Murine cDNA sequence encoding the CRAM-1 (SEQ ID NO:11) and CRAM-2 (SEQ ID NO:12) proteins. muCRAM-1 was subcloned in pcDNA3 vector and sequenced using Sp6 and 17 primers. muCRAM-2 was obtained as IMAGE clone from EST library (Ac: AA690843 and W80145) and was sequenced in the pT7T3-DPac vector using 17 and T3 primers.

Figure 2B:
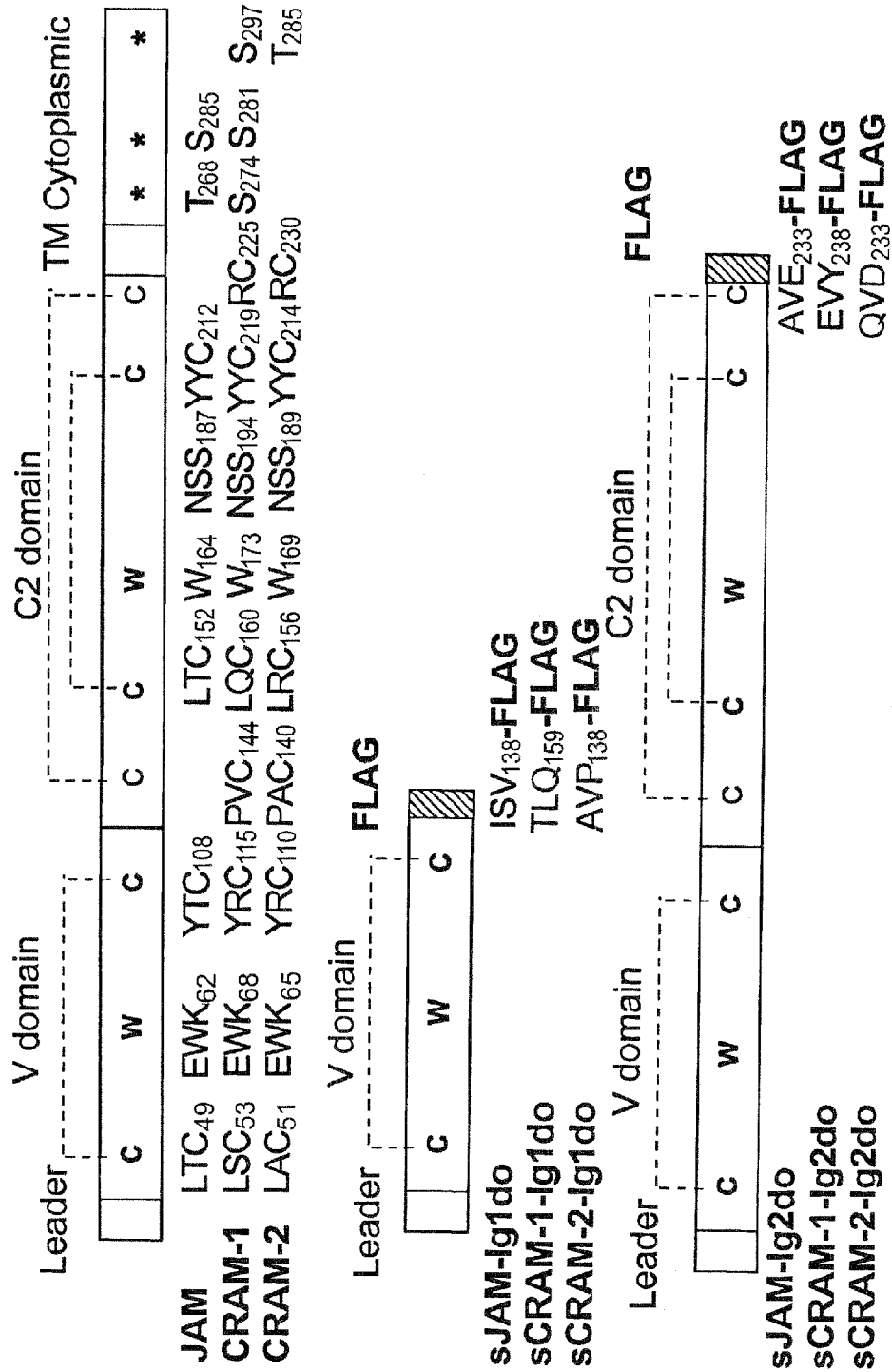

FIG. 2: Schematic representation of the molecular tools used in the example. The structure and important residues of the new family are depicted in the upper top panel. The stars represent the putative phosphorylation sites in the cytoplasmic part of the three molecules. The second canonical Cys residue of the C2 domain is missing in the JAM sequence. Different chimeric molecules are represented below with the position and the surrounding residues of the fusion sites. Part of the molecules originating from JAM, CRAM-1 or CRAM-2 sequences are shown in white background.

FIG. 3: Alignment of CRAM-1 (top; SEQ ID NO:13) and CRAM-2 (bottom; SEQ ID NO: 14) amino acid sequences. Gaps are indicated as dashed.

FIG. 4: Alignment between murine (top; SEQ ID NO: 13) and human (bottom; SEQ ID NO:15) CRAM-1 (JAM-2).

FIG. 5: Alignment between murine (top; SEQ ID NO: 14) and human (bottom; SEQ ID NO:16) CRAM-2 (JAM-3).

FIG. 6: Nucleic acid sequence of human CRAM-1 (FIG. 6A; SEQ ID NO:17), complete amino acid sequence of human CRAM-1 (FIG. 6B (top); SEQ ID NO:15), and partial amino acid sequence of human CRAM-2 (FIG. 6B (bottom); SEQ ID NO:16).

FIG. 7: Targeted differential display using degenerated primers. (A): Nucleotide sequences of PCR primers (tayagntgynnngcytcyaa (SEQ ID NO: 1): taycrgtgynnngcytcyaa (SEQ ID NO:2); taytaytgynnngcytcyaa (SEQ ID NO:3); tayagntgynnngcyagyaa (SEQ ID NO:23); taycrgtgynnngcyagyaa (SEQ ID NO:24); and taytaytaynnnacyagyaa (SEQ ID NO:25) encoding the sequences present in C2 Ig domains (SEQ ID NOS: 18-20) are shown. Two primers encode the same sequence due to the codons encoding Ser residue. The level of degeneracy is 4096 different forms for the primers encoding YRCXAS (SEQ ID NO:18) and 2048 forms for the others ((YQCXAS (SEQ ID NO: 19) and YYCXAS (SEQ ID NO:20)). (B): The display of radioactive PCR products obtained with the YYCXAS1 (SEQ ID NO:20) primers is shown. The lanes correspond to the display of PCR product run on cDNA obtained from the t-end endothelial cell line (lane t-end), the B16 melanoma cell line (lane B16), or the co-culture between the two cell lines (central lane). The arrow indicates the PCR product of interest obtained from down-regulated transcript CRAM-1 under co-culture condition.

Figure 8D:
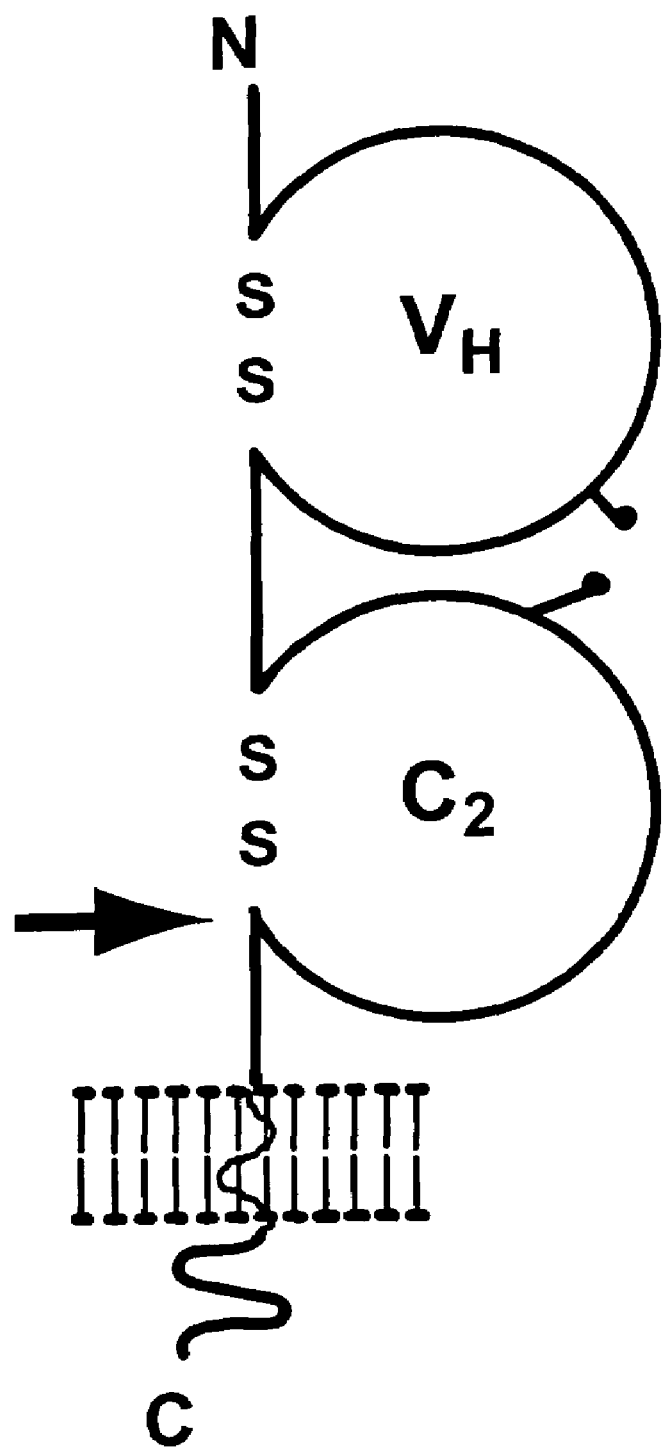

FIG. 8: (A) Nucleotide (SEQ ID NO: 32) and deduced amino acid (SEQ ID NO: 33) sequence of Confluency Regulated Adhesion Molecule 1 (CRAM-1) cDNA. The putative hydrophobic signal peptide (first) and transmembrane region (second) are underlined. Predicted N-glycosylation sites (strikeout), cysteines likely to form disulfide bonds (brackets) and Ser/Thr/Tyr residues of possible phosphorylation sites (bold) are indicated. (B) Structural model for murine CRAM-1 protein. Extracellular part showing a VH and a C2 like Ig domain with two putative N-linked glycosylation sites. The arrow points to the region targeted by the partially degenerated primers (YYCXAS1) (SEQ ID NO: 20) used in the Targeted Differential Display.

FIG. 9: JAM (SEQ ID NO:21), CRAM-1 (SEQ ID NO:13), and CRAM-2 (SEQ ID NO: 14) murine protein sequence alignment. The identical residues are boxed in black and the homologous residues are shaded in gray. The overall identity is 36% between CRAM-2 and CRAM-1, 31% between JAM and CRAM-1 and 33% between JAM and CRAM-2; the respective homologies are 52%, 52% and 49%. The gaps are shown by dashes in the sequences. The canonical conserved residues (Cys and Trp) of the V and C2 domains are marked by an asterisk.

FIG. 10: Expression of transcripts encoding JAM, CRAM-1 and CRAM-2 detected by RT-PCR in different lines (A) or detected by Northern blot in various tissues (B) (A): RT-PCR is achieved on cDNA originating from endothelial cell line treated by TNF (lanes 2 and 11 correspond to TNF treated t-end) or not treated (lanes 3, 4, 6, 7, 9, 12 correspond to b-end.5, e-end.2, t-end $V^{++}L^-$, t-end $V^{low}L^{++}$, TME and t-end, respectively). Lanes 5 and 10 correspond to the tumor cell lines B16 (melanoma) and KLN205 (carcinoma). Lane 8 corresponds to the non transformed thymic epithelial cell line MTE4-14. Lane 1 is the positive control for JAM, CRAM-1 and CRAM-2 amplifications on the plasmids containing the cloned cDNAs. (B): Autoradiograph of $P^{32}$ probe hybridization to mouse Northern blot. The probes used for each hybridization are indicated left. The hybridization signals for JAM and CRAM-1 are detected at the size of 2 kb.

FIG. 11: JAM-2 and JAM-1 localization to established cell-cell contacts. A; Immunocytochemistry was performed on paraformaldehyde fixed TME cells with anti-JAM-2 (a) or anti-JAM-1 (b) antibodies. Arrows indicate the specific localization of the proteins to cell-cell contacts. Bar, 10 μm. B: JAM-2-EGFP (a) and JAM-1-EGFP (c) chimeric molecules were specifically localized to cell contacts between transfected cells. The enrichment in EGFP recombinant proteins was not observed between transfected and non-transfected cells (arrowhead). Bar, 20 μm. C: Immunoprecipitation of JAM-2 after surface biotinylation of TME endothelial cells. Anti-PECAM (lane 1) and anti-JAM-1 (lane 2) antibodies were used as negative and positive controls respectively for the immunoprecipitation with CRAM-XIXH36 antibody (lane 3). Molecular weights are indicated on the right. D: Immunoprecipitation of EGFP recombinant proteins from CHO transfected cells. Anti-JAM-2 (lanes 2, 3, 6), anti-JAM-1 (lanes 1, 4, 5) were used to immunoprecipitate the biotinylated lysates from untransfected (lanes 1 and 2), JAM-1-EGFP (lanes 3 and 4), or JAM-2-EGFP (lanes 5 and 6) transfected CHO cells. Molecular weights are indicated on the right.

Figure 12:
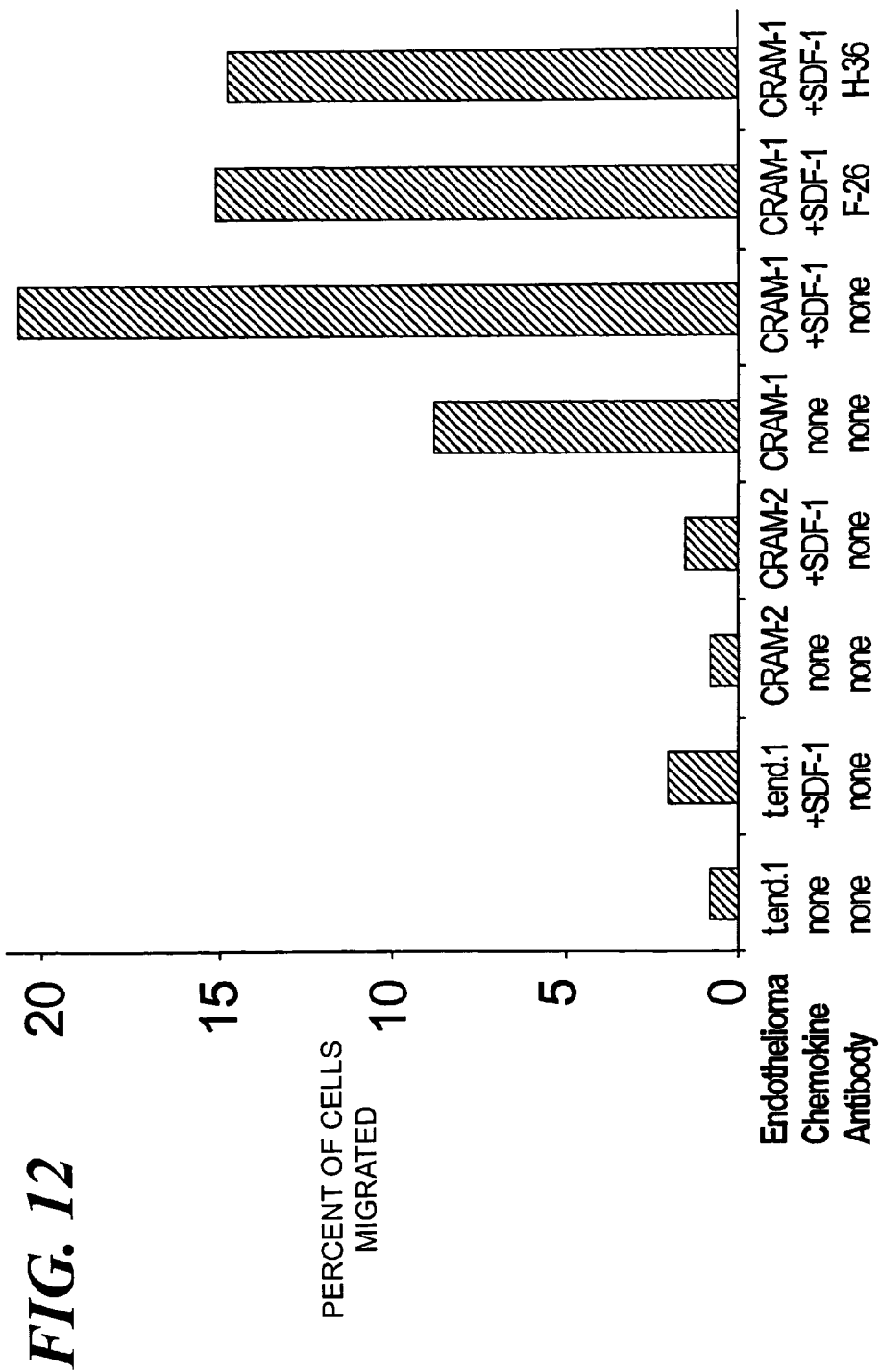

FIG. 12: Migration of splenocytes across monolayers of TNF-activated endotheliomas, in the presence or absence of the chemokine SDF-1. Three endotheliomas were used: wild-type t.end.1, or t.end.1 transfected with the cDNA encoding for CRAM-1 or CRAM-2. Two monoclonal antibodies were tested for their ability to affect transmigration, F-26 or H-26, both rat IgGl monoclonal antibodies directed against murine CRAM-1.

Figure 13:
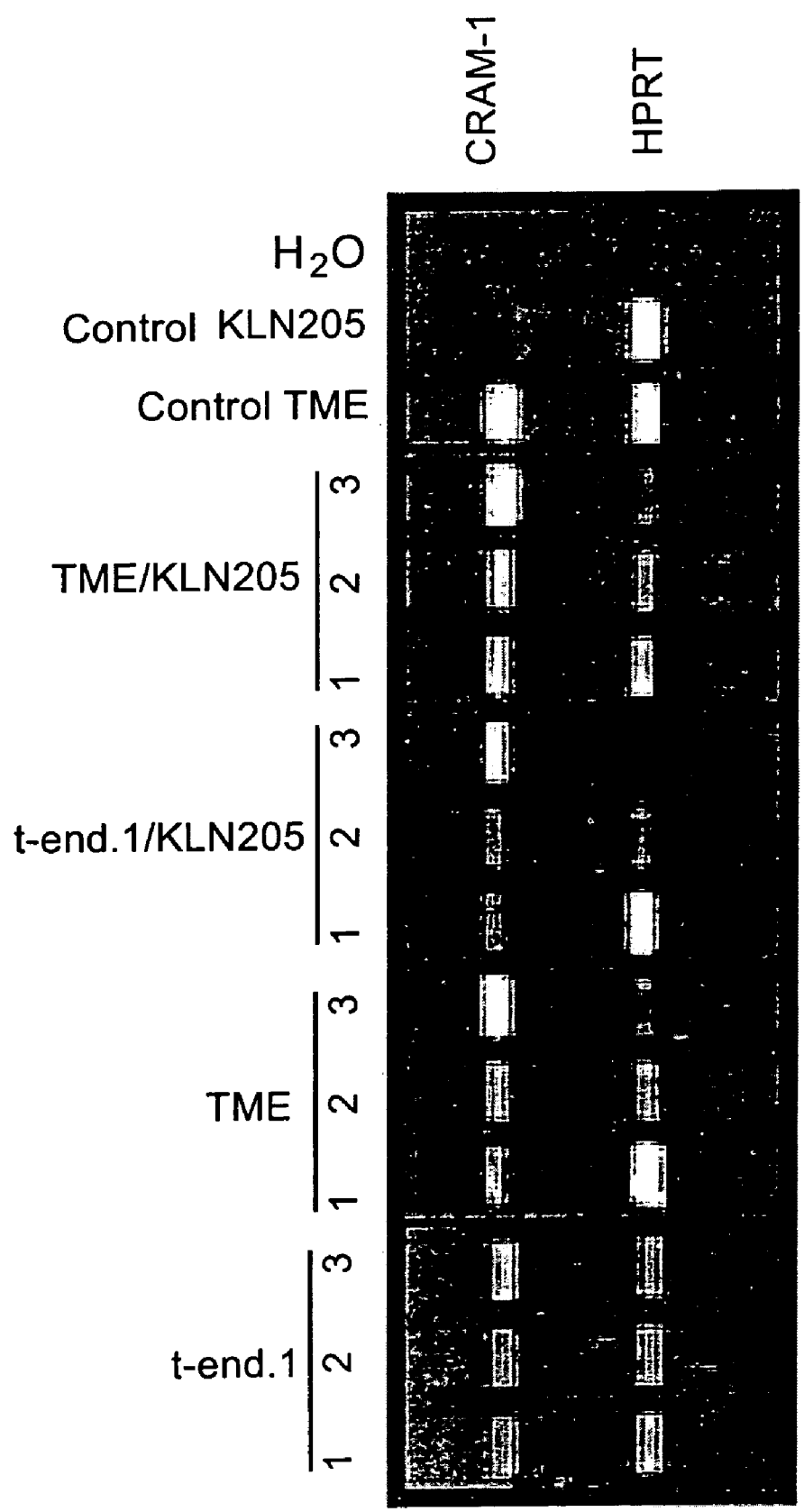

FIG. 13: CRAM-1 regulation in function of confluency. The semi-quantitative PCR is driven using a mix of primers specific for HPRT and the CRAM-1 cDNAs. The PCR reactions are run on a 1.2% agarose gel and stained with ethydium bromide. Lanes 1, 2 and 3, correspond to 100, 50 and 10% confluency respectively. A weaker signal for CRAM-1 in the 100% confluency (lane 1) is observed. The culture condition of the endothelial cell lines (t-end.1 and TME) on their own or mixed with the tumor cell line KLN 205 is indicated.

FIG. 14: Northern blot analysis of JAM-2 (a), JAM-1 (b) or β-actin (c) transcripts in mouse tissues. Results on embryonic post-coitum (pc) and adult mRNA preparations are shown. The sizes of the hybridization signals are indicated on the right.

Figure 15:
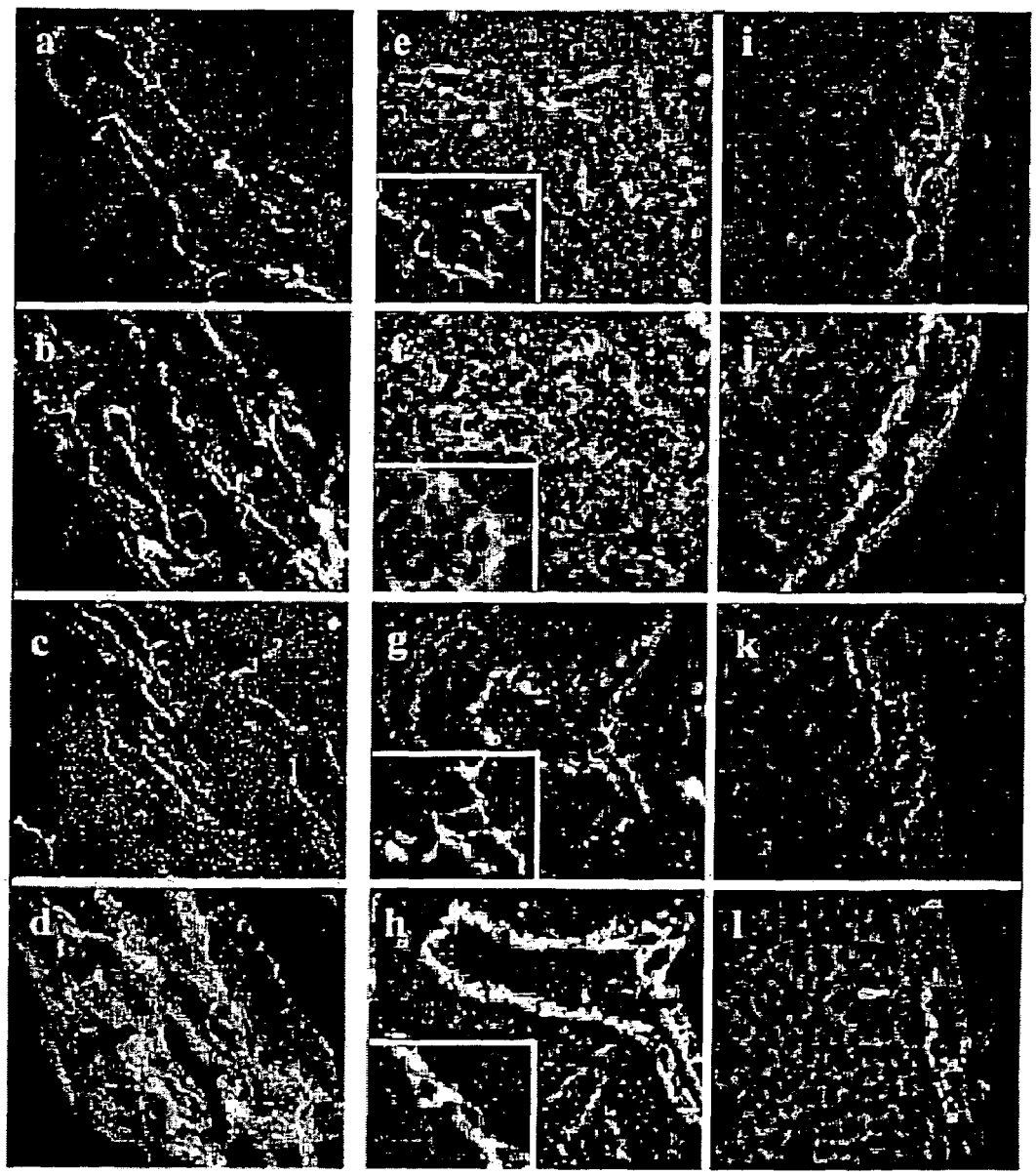

FIG. 15: Immunohistological analysis of JAM-2, JAM-1, ZO-1 and PECAM expression. Serial sections of kidney (a-d) or sections from mesenteric lymph node (e-l) were stained with anti-JAM-2 (a, e, i), anti-JAM-1 (b, f, j), anti-ZO-1 (c, g, k) or anti-PECAM (d, h, l) antibodies. Each series of pictures (a-d, e-h, and i-l) were acquired with identical settings for the CCD.

FIG. 16: JAM-2 expression on endothelial cells. A: Cytofluorimetric analysis of JAM-2, JAM-1, and PECAN expression on endothelial cell lines (tEnd.1, eEnd.2 and TME) or squamous carcinoma cell line (KLN 205). Dashed profiles represent the negative controls obtained with an antibody directed against CD4. B: Cytofluorimetric analysis of JAM-2 on freshly isolated endothelial cells. Indicated organs were dissociated by Collagenase/dispase digestion, stained with DiIAc-LDL, CD31 and anti-JAM-2 or anti-JAM-1 as indicated. Histogram profiles were obtained by gating endothelial cell population positive for DiIAc-LDL (FL-2) and CD31 (FL-3). Negative controls were obtained by omitting the primary mAbs against JAM-1 or JAM-2.

FIG. 17: (A): JAM-2-EGFP localization during cell-cell contact formation. Single fluorescence pictures were collected every 3 min for 1 hour during the monolayer formation of CHO cells transfected with JAM-2-EGFP. Pictures obtained during the first 18 min are shown. At time 0, asterisks identify the three cells present on the field. At time 6, 12 and 18 min, arrows highlight the relocalisation of JAM-2-EGFP to the newly formed cell-cell contact. (B): JAM-2-EGFP localization after wounding. Arrows indicate the wounded side and arrowheads highlight the membrane processes rich in JAM-2-EGFP. Elapsed time is indicated on the pictures. Bar, 10 µm.

Figure 18:
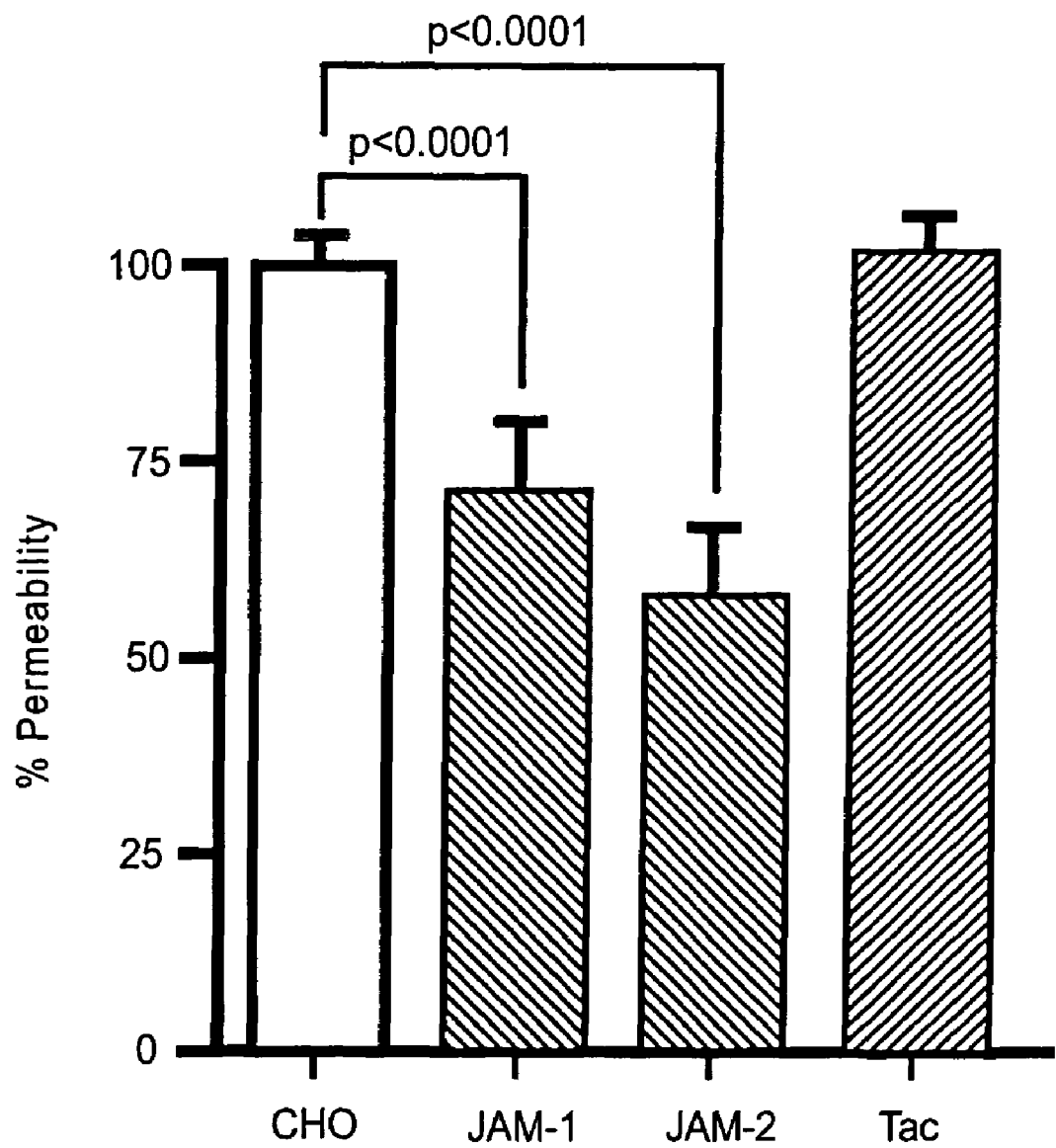

FIG. 18: JAM-2 expression decreases paracellular permeability. (A): Paracellular permeability was evaluated by FITC-Dextran diffusion across non transfected CHO cell monolayers, CHO cells transfected with Tac (huIL2Rα) or with the indicated EGFP fusion protein (JAM-1 or JAM-2). Transfection of JAM-2-EGFP or JAM-1-EGPP in CHO cells led to a significant decrease in paracellular permeability (57.8%$^+$/−4.9 and 70.8%$^+$/−3.6 respectively, p<0.0001), whereas transfection of Tac did not significantly affect the paracellular permeability (100.4%$^+$/−4.4, p=0.9872). Results were normalized to non-transfected CHO cells.

FIG. 19: Targeting of JAM-2-EGFP (A) and JAM-1-EGFP (B) to preexisting tight junctions. Confluent MDCK cells, stably transfected with JAM-2-EGFP (A), or JAM-1-EGFP (B), were stained with anti-occludin and anti-rabbit-Texas/Red. Series of pictures every 0.9 µm from basal to apical levels are shown for EGFP fluorescence (a) or occludin staining (b). The basal level on the left was arbitrary defined such as the serial pictures comprise the tight junctional level on focus at +3.6 and +4.5 µm (fourth and fifth pictures to the right).

FIG. 20: Effect of soluble recombinant molecules on leukocyte transendothelial migration. (A): Transmigration is expressed as a relative index and normalized on the values obtained on the non-treated t-end cell line (dashed line Index 1). Results obtained in the presence of 1 µg sJAM-I2do (open squares) or in the presence of 1 µg sCRAM-1-Ig2do (filled circles) are shown. Index is calculated as a mean of five independent transmigration experiments. (B): Phenotype of transmigrated cells is expressed as cell numbers calculated from the percentages obtained by Facs analysis following staining with anti CD3-FITC and anti B220-PE. The stars indicate the experimental points with a significant difference to the control.

In the examples the terms JAM and JAM-1, CRAM-1 and JAM-2, as well as CRAM-2 and JAM-3 may be used interchangeably.

EXAMPLE

MATERIALS AND METHODS

Cell Lines

The thymic (tEnd.1), and embryonic (eEnd.2) endothelioma cell lines (Williams et al., 1989, *Cell* 57:1053-1063) were provided by Dr. W. Risau and Dr B. Engelhardt (Max Planck Institute, Bad-Nauheim, Germany). The SV40 transformed lymph node endothelial cell line TME was provided by Dr A. Hamann (Harder et al., 1991, *Exp Cell Res.* 197: 259-267). The squamous cell carcinoma KLN 205, the CHO, the MDCK, and the myeloma cell line Sp2/0, were obtained from the American Type Tissue Culture Collection (ATCC). All cells, except CHO, were grown in DMEM (Gibco BRL, Paisley, Scotland), supplemented with 10% FCS (PAA Laboratories, Linz, Austria), 2 mM Glutamine, 100 U/ml Penicillin and 100 U/ml Streptomycin (all Gibco BRL) CHO cells were grown in Nut.Mix.F-12 (HAM) medium supplemented as above. Adherent cells were detached by washing with PBS/0.15 mM EDTA followed by 5 min incubation in trypsin/EDTA at 37° C.

Display, Cloning and Sequence Analysis

For co-culture experiments, 5×10$^5$ t.End.1 cells were grown together with 2.5×10$^4$ B16 F10 melanoma cells for 64 hours in 10 cm tissue culture dishes. As control, 5×10$^5$ t.End.1 and 2.5×10$^5$ B16 F10 cells were grown separately under the same conditions resulting in confluent monolayers after 64 hours. Total RNA was directly extracted in petri dishes with Trizol reagent following manufacturer's instructions (Gibco BRL, Paisley, Scotland). The cDNA was prepared from 5 µg of total RNA, employing oligo-dT (16-mer) primer and Superscript Reverse Transcriptase (Gibco BRL, Paisley, Scotland). The quality and quantity of cDNA were checked by running 27 cycles of PCR on 1 µl of cDNA diluted 1:5, using primers specific for the housekeeping HPRT cDNA. Then the differential PCR was performed with the following degenerated $^5$'TAYAGNTGYNNNGCYTCYAA$^3$'(SEQ ID NO:1), $^5$'TAYCRGTGYNNNGCYTCYAA$^3$ '(SEQ ID NO:2'), and $^5$'TAYTAYTGYNNNGCYTCYAA$^3$'(SEQ ID NO:3) encoding for the most frequent amino acid sequences encountered in the C2 domains: YRCXAS (SEQ ID NO: 18), YQCXAS (SEQ ID NO:19), and YYCXAS (SEQ ID NO:20). The PCR conditions consisted gf using: 2 µl of diluted cDNA; 2.5 µl of 10X Goldstar PCR buffer; 2 µl of MgCl$_2$; 2 µl of degenerated primers 0.3 mM; 0.5 µl of dNTP 0.1 mM; 0.1 µl of αP$^{33}$ dATP 10 mCi/ml (Amersham Pharmacia Biotech, Dubendorf, Switzerland); 15.65 µl H$_2$O; 0.25 µl Goldstar Taq polymerase (Eurogentech, Seraing, Belgium).

The parameters for the PCR were as follows: 45 sec at 94° C., 90 sec at 50° C., and 45 sec at 72° C. repeated 40 times. Formamide/EDTA loading buffer was added and samples were denatured for 2 min at 94° C. The PCR products were then separated on a 6% polyacrylamide gel, and autoradiographed using Kodak OM-Mat. The band intensities were compared.

Differentially expressed bands were cut from the dried polyacrylamide gel and fragments were retrieved by boiling and ethanol precipitation as previously described (Liang and Pardee, 1992, *Science.* 257:967-970). The PCR products were then reamplified using increased concentrations of dNTPs (0.2 mM instead of 2 µM) without P$^{33}$-ATP. The products of re-amplification were cloned into pGem-T Easy Vector (Promega Corp, Wallisellen, Switzerland) as described previously (Sambrook, Fritsch, and Maniatis; Molecular cloning; 2$^{nd}$ed; Cold Spring Harbor Laboratory Press; 1989).

Nucleic acid sequences of two independent clones were determined using the Thermo Sequence Fluorescent Labeled Primer Cycle Sequencing Kit (Amersham Pharmacia Biotech, Dübendorf, Switzerland) and the LJ-COR DNA Analysis System (MWG-Biotech GmbH, Ebersberg, Germany).

Identification of JAM-3

Sequence analysis and comparison were performed via the applications available on the ExPASy Molecular Biology Server i.e. Blast, Prosite, Swiss-Prot. Three different ESTs homologous to CRAM-1 were identified (Accession No.

AA726206, AA052463 and AA175925). None of them encoded for a full length transcript and comprised the initiating ATG sequence. Therefore, the 5' coding sequence was obtained using the 5'RACE-PCR System for Rapid Amplification of cDNA Ends, Version 2.0 according to manufacturer's instructions (Gibco ORL, Paisley, Scotland).

The three primers used were designed based on the EST sequences as follows: 5'-GAGGTACTTGCATGTGCT-3' (SEQ ID NO:4) for the synthesis of the first strand, 5'-CGACAGGTGTCAGATAACA-3' (SEQ ID NO:5) and 5'-CACCCTCCTCACTCGT-3' (SEQ ID NO:6) for the two nested PCRs. The 5' RACE-PCR product was cloned into pGem-T Vector. To obtain the full length coding sequence for CRAM-i, the cloned 5' RACE-PCR product and the EST (accession No. AA726206) were digested with HpaI and NotI restriction enzymes and ligated into pGem-t vector. Cloning of full length CRAM-2 was based on the same strategy of sequence comparison and 5' RACE technique. The full-length cDNA encoding CRAM-2 was finally obtained from ESTs accession numbers: AA690843 and W80145. These two clones differ by the length of the 3' untranslated region.

Northern Blot

Total mRNA from cells or tissues was extracted using Trizol (Life technologies A G, Basel, Switzerland) according to manufacturer's instructions. Poly-A+ mRNA was extracted from 250 µg total RNA with the Oligotex mRNA Purification Kit (Qiagen, Zurich, Switzerland). Embryonic Poly-A northern blot was purchased from CLONTECH (P. H Stehelin and Cie A G, Basel, Switzerland). The riboprobes were prepared from pcDNA3 vector (Invitrogen, Leek, Netherlands), and comprised the sequences encoding for the immunoglobulin domains of JAM-1 and JAM-2, or the full-length coding sequence for β-actin. Hybridization was performed at 62° C. in buffer containing 50% formamide. The blots were then washed twice (0.5×SSC, 0.1% SDS, 67° C.), and autoradiographed on Kodak X-Omat at −80° C.

Confluence Experiment

The effect of endothelial cell confluency on JAM-2 mRNA levels was investigated. $2 \times 10^5$ TME endothelial cells were cultured in 6, 10, and 15 cm diameter culture dishes to reach different levels of confluency after 64 hours ranging from 10 to 100%. The number of cells after. 64 hours, checked by trypan blue exclusion and counting, was the same in all cases, and was not related to the surface area of the petri dish.

Semi-quantitative PCR reaction or northern blotting were used to determine relative amount of transcript in the various conditions. For the detection of the JAM-2 transcript, the 5'-GACTCACAGACAAGTGAC-3'(SEQ ID NO:7) and 5'-CACCCTCCTCACTCGT-3'(SEQ ID NO:8) primer pair was used, giving a 750 bp amplification product. As internal control, the following primers specific for Hprt cDNA were used to amplify a 350 bp long fragment: 5'-GTTGGATACAGGCCAGACTTTGTTG-3'(SEQ ID NO:9) and 5'-GAGGGTAGGCTGGCCTATAGGCT-3'(SEQ ID NO:10).

```
5'-GTTGGATACAGGCCAGACTTTGTTG-3'
(SEQ ID NO:9) and 5'-

5'-GAGGGTAGGCTGGCCTATAGGCT-3'
(SEQ ID NO:10).
```

Construction of Expression Vectors

The sequence encoding EGFP was subcloned from pEGFP-1 vector (CLONTECH, P. H Stehelin and Cie A G, Basel, Switzerland) into pcDNA3 using HindIII and NotI sites, therefore named pcDNA3/EGFP. The 3' restriction sites, HpaI and ScaI, found in the sequence encoding respectively the cytoplasmic domain of JAM-2 and JAM-1, were used to fuse the two sequences at the N-terminus of the EGFP in pcDNA3 vector (Invitrogen, Leek, Netherlands). The inserts encoding JAM-2 or JAM-1 were excised from pGemt or pRc/CMV using SacII/HpaI or HindIII/ScaI digestions, respectively.

The coding sequences were then cloned in pcDNA3/EGFP vector digested with AgeI, blunted by fill-in and further digested with HindIII or SacII enzymes. This resulted in fusion sites at amino-acid positions $DGV_{291}$ for JAM-2 and $QPS_{285}$ for JAM-1. The transfection of CHO cells was performed as previously described (Ballestrem et al., 1998, *J Cell Sci.* 111:1649-1658).

Stable transfectants used for permeability assays were selected by growing transfected CHO cells for two weeks in medium containing 1 mg/ml of G418. Resistant colonies were isolated and checked for EGFP fluorescence intensity by flow cytometry (FACScalibur apparatus, Becton Dickinson, Mountain View, Calif.) and fluorescence localization by microscopy (Axiovert, Zeiss, Oberkochen, Germany).

Time-lapse video microscopy was performed using an Axiovert fluorescence microscope and Openlab software for image acquisition.

The mammalian expression vector pcDNA 3 (Invitrogen, Leek, Holland) was modified by integrating the Flag-Tag (G. Wiedle, Dep. of Pathology, CMU, Geneva) coding sequences. Flag-Tag constructs containing coding sequences for the soluble forms of the JAM, CRAM-1 and CRAM-2 proteins were prepared by PCR. In all cases, the forward primers were designed to fit ATG initiation region. The reverse primers were designed in the sequences encoding the hinge region for the one Ig soluble form or in the sequence encoding the region between the C2 and transmembrane domains for two Ig domains soluble molecules. All reverse primers had 3+ extensions containing a XbaI restriction Bite for direct in-frame cloning in the Flag-tag modified vector. Pfu DNA polymerase was employed in the PCR to avoid frequent mutations (Stratagene, La Jolla, Calif., USA). The PCR fragments were then digested with XbaI and cloned into the pcDNA-3 Flag-Tag vector, digested by EcoRI, filled by Klenow and followed by an XbaI digest.

Reagents and Immunofluorescence Analysis

The following monoclonal antibodies were used: anti-PECAM (GC51, rat $IgG_{1a}$; EA-3, rat $IgG_1$) and anti-JAM (H202.106.7.4, rat $IgG_1$) (Malergue et al., 1998, *Mol Immunol.* 35:1111-1119.; Piali et al., 1993, *Eur J Immunol.* 23:2464-2471).

The panel of CRAM antibodies against JAM-2 was generated in the laboratory using standard techniques, and recombinant soluble molecule as immunogen (Aurrand-Lions et al., 1996, *Immunity.* 5: 391-405). The selected hybridomas were screened by ELISA for the production of antibodies recognizing specifically the recombinant soluble JAM-2 molecule. Positive clones were further tested on CHO cells transfected with JAM-2 cDNA (not shown).

All CRAM antibodies are of the $IgG_1$ or $IgG_{2a}$ isotype except CRAM-25F24, which is of the $IgG_{2b}$ subclass. Antibodies were purified on Protein G sepharose columns (Pharmacia Biotech Europe, Dübendorf, Switzerland) according to the manufacturer instructions. CRAM-19H36 mAb was used for immunoprecipitation, whereas CRAM-18F26 was the reagent used for immunohistochemistry. Similar results were obtained with CRAM-4H31 and CRAM-17D33 mAbs.

Immunofluorescence analysis was performed using secondary reagents coupled to FITC or Texas Red (Jackson Immunoresearch, Milan A G, La Roche, Switzerland) for cytofluorimetry and immunohistochemistry, respectively.

For immunohistochemistry, samples were fixed 5 min with cooled (−20° C.) methanol. Samples were rehydrated in PBS, gelatine 0.2%, Tween 20 0.05%, incubated overnight with the primary antibodies before washing, and revealed with the appropriate secondary reagent coupled to Texas Red. For the analysis of fresh endothelial cells, dissociation of freshly dissected tissues was performed using collogenase/dispase digestion, according to established procedures (Kramer et al., 1984, *J Cell Biol.* 99:692-698). The dissociated cells were stained for 2 hours at 37° C. with DiI-Acetylated LDL (Molecular Probe Europe BV, Leiden, Netherlands) before staining with anti CRAM-19 and goat anti rat-FITC probe. After three washes, cells were stained with biotinylated anti-CD31 (Pharmingen) and streptavidine Red 670 (Life technologies A G, Basel, Switzerland).

JAM-1 or JAM-2 expression was analyzed on cells positive for the two endothelial cell markers: Acetylated-LDL (FL-2) and CD31 (FL-3). Negative controls were obtained by omitting primary antibody.

Immunoprecipitations

Immunoprecipitations were performed as previously described (Aurrand-Lions et al., 1997, *Cellular Immunology.* 176:173-179) using 10 MM Tris-HCl buffer pH 7.4, 150 mM NaCl, 0.5% Triton X100, 0.5% NP40, protease inhibitor cocktail (Roche Diagnostics Ltd, Rotkreuz, Switzerland) for lysis. After immunoprecipitation, SDS/PAGE, and transfer to nitrocellulose membrane, the biotinylated proteins were revealed using streptavidin coupled to peroxidase (Jackson Immunoresearch) and ECL (Amersham Pharmacia Biotech, UK).

Permeability Assays

Permeability was measured using Transwell chambers (6.5 mm diameter, PC filters, 0.4 μm pore size, Costar Corp). In brief, $1\times10^4$ transfected or non-transfected transfected CHO cells were cultured to confluency on filters previously coated for 30 min with 0.2% gelatin. After 5 days, the medium was changed for prewarmed Nut/F12 medium without FCS (500 μl in the lower chamber and 200 μl in the upper chamber). FITC-dextran (MW 38.900, Sigma Chemical Co) was added in the upper chamber at 1 mg/ml final concentration.

After 1 hour, chambers were removed and fluorescence was read directly in the lower chamber using Cytofluor II. The mean fluorescence intensity of five independent chambers was calculated and compared using Statview software and t-test unpaired comparisons. To normalize experiments, the value of mean fluorescence intensity obtained with wild type CHO cells was taken as 100%.

Transfection and Purification of Soluble Molecules

Transient transfection of 293 T. Bosc 23 or stable transfection of CHO cells with the soluble Ig1Do and Ig2Do Flagtag/pcDNA-3 constructs were carried out using Lipofectamine Reagent according to manufacturer's instructions (Gibco BRL, Paisley, Scotland). Following transfection supernatants were collected every two days during a ten days period. M2 Beads (Kodak, New Haven, USA) covalently linked to anti-Flag antibody were washed twice with PBS containing a Protease Inhibitor Mix (Boehringer Mannheim, Germany). The beads were then incubated at 4° C. for 3 hours with supernatant from the transfected cells. After five washes with PBS containing protease inhibitors, a column was packed with the beads, and recombinant molecules were eluted with 10 mM glycine buffer pH 3.4 according to the manufacturer. The eluted fractions containing the recombinant proteins were then concentrated on Centricon-10 (Millipore) and dialyzed against PBS.

Final protein concentration was determined using the Micro BCA assay (Biorad). The purified products were then submitted to a polyacrylamide SDS gel electrophoresis followed by coomassie blue staining to analyze their purity.

Transmigration Assays

Leukocyte transmigration across endothelial cells was performed as previously described (Wheerasinghe et al., 1998, *J. Cell Biology,* 142; 595-607). Briefly, $1\times10^5$ t-end cells were cultured for two days in transwell units (polycarbonate filters, 5 μm pore size, costar) in the presence of 1 μg of Ig soluble recombinant molecules: sJAM 2do or sCRAM-2do. After two days, $1\times10^6$ leukocytes obtained from lymph nodes and Peyer's patches were added to the upper compartment, and the number of transmigrated cells was monitored during the experiment every hour. After 4 hours, transmigrated cells obtained from five independent wells were pooled and submitted to cytofluorimetric analysis for B- and T-cell markers B220 and CD3. Results were obtained using a Facscalibur machine and the Cell-Quest analysis program (Becton-Dickinson).

For a transmigration assay with splenocytes, $3\times10^5$ endothelial cells were seeded in transwell units (polycarbonate filters, 8 μm pore size, costar) allowing the cells to form a monolayer over 18 hours. Medium in the upper compartment was removed and $1\times10^5$ leukocytes in 100 μl, freshly prepared from spleen by Ficoll centrifugation, were added to the upper compartment. SDF-1 was added to the medium (final concentration: 40 nM) in the lower compartment to establish a chemokine gradient between lower and upper compartments. For the experiment with antibodies, purified antibodies 18-F26 or 19-H36 were added at the concentration of 10 μg/ml in the upper compartment with splenocytes. After 4 hours, transmigrated leukocytes (in the lower compartment) were harvested and: counted. Results were expressed as % of input.

RESULTS

Targeted Differential Display

The regulation of genes in endothelial cells depends on their environment. The present invention was directed to the identification of genes that undergo regulation upon the contact of endothelium with tumor cells. For this purpose, an in vitro assay was developed using the co-culture of melanoma tumor cells (B16) with an endothelioma cell line (t-end). Total RNA extracted from the mix was used as template to prepare cDNA submitted to a differential PCR screen. The cDNA obtained from the endothelial or melanoma cells cultured on their own were used as controls. The three different patterns were compared to identify the transcripts regulated by the co-culture condition. To limit the analysis to the sequences encoding for cell surface molecules of Ig superfamily, partially degenerated primers were used that target the sequence surrounding the C-terminal cysteine of C2 domains in Ig superfamily molecules. The most reproducible pattern of PCR products was obtained using primers that encode the sequence YYCxAS1 (FIG. 7A; SEO ID NO:20). This improved method of RNA display technique was named TDD for "Targeted Differential Display".

Figures 7A, 7B:
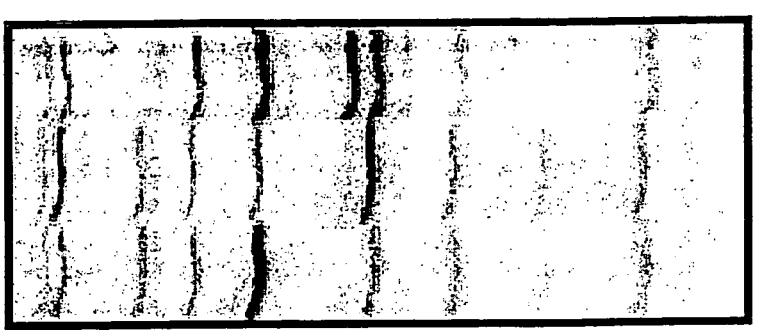

In repeated experiments of TDD, sixteen differentially expressed genes were identified. Following cloning, nucleotide and amino acid sequence analysis, three of the sixteen PCR products were possible candidates encoding for unknown members of the Ig superfamily. One of the three candidates (CRAM-1) was chosen for further investigation. When grown separately, t-end. 1 endothelial and B16 melanoma cells expressed high levels of the CRAM-1 transcript. However, under co-culture conditions the level of CRAM-1 expression was down regulated (FIG. 7B). Translation of a 350 bp long fragment corresponding to CRAM-1 showed the amino acid sequence YYCxAS (SEQ ID) NO:20) indicating the endings of an Ig C2 domain followed by an open reading frame (ORF) containing a hydrophobic stretch of 18 amino-acids that signed a transmembrane region.

CRAM-1, a Member of the Immunoglobulin Superfamily

Sequence comparison between the PCR product sequence and nucleotide databases revealed homologous and identical sequences in mouse ESTs databases. The presence of ESTs indicated that the PCR product corresponded to a sequence expressed in vivo. Three ESTs were found to contain a 300 bp long sequence at their 5' end, which was identical to 300 bp in the TDD product. The 3' ends of each EST contained a poly-A tail. In total the ESTs were 1270 bp in length and corresponded to the 3' end of the CRAM transcript. Since the 5' end of the transcript was missing in the EST cDNA clone, it was obtained by 5'RACE-PCR. The resulting 1980 nucleotide long full length coding sequence of the postulated CRAM-1 cDNA is shown in FIG. 8A. There was a strong consensus site (GACATGG) for translation initiation 16 bp downstream from the 5' end, followed by a single ORF predicting a protein of 310 amino acid. The 31 amino-acid region subsequent to the potential initiating methionine, was characteristic of a signal peptide. The cleavage site was predicted to be at Ala 31-Val 32.

The putative structure of the murine CRAM-1 protein is shown in FIG. 8B and consists of an extracellular region with a variable heavy chain arid a constant type 2 like immuno-globulin domain (Pfam, The Sanger Centre and Blast) with two potential N-linked glycosylation sites (aa 104 and 192). The hydrophobicity analysis (Tmpred, ISREC) predicted a transmembrane region between positions 242-260. The postulated cytoplasmic domain consisted of 49 amino acids and contained a number of highly conserved Ser/Thr and Tyr phosphorylation sites (FIG. 8A, residues in italic). The search of known patterns with the Prosite program identified the motifs SSKISYK as protein kinase C, SKQD/TSEE (SEQ ID NOS:27-28) as CK2 and KQDGESY/KHDGVNY (SEO ID NOS:29-30) as Tyrosine kinase phosphorylation signatures.

JAM, CRAM-1 and CRAM-2 Define a New Subfamily

Several proteins showed high homology to CRAM-1. Two members of the Ig Superfamily: Human A33 antigen and part of the mouse neural cell adhesion molecule, N-CAM were found to have 41% and 46% homology with CRAM-1 respectively. JAM, another member of the Ig Sf, had a similar structure as CRAM-1 with 34% amino acid sequence identity, and 54% homology. The significant identity between JAM and CRAM-1 was used to find a third closely related sequence in EST databases, namely CRAM-2. The identity between the three molecules suggested the existence of a new subfamily of molecules in the Ig superfamily (FIG. 9). The homology concerned not only the overall structure of V and C2 domains (C54 to C118 and C147 to C235 in FIG. 9) but also sequences inside the cytoplasmic domains. Interestingly, the most divergent regions between the three molecules were found at the beginning of the V domain (position 40 to 60) and in the proximal cytoplasmic part (position 280 to 300). The functions of these two regions correspond to sequences involved in ligand binding and signal transduction in other members of the Ig superfamily suggesting a role of JAM, CRAM-1 and CRAM-2 in cell-cell communication.

Tissue Distribution of JAM, CRAM-1 and CRAM-2 mRNA

Figure 10A:
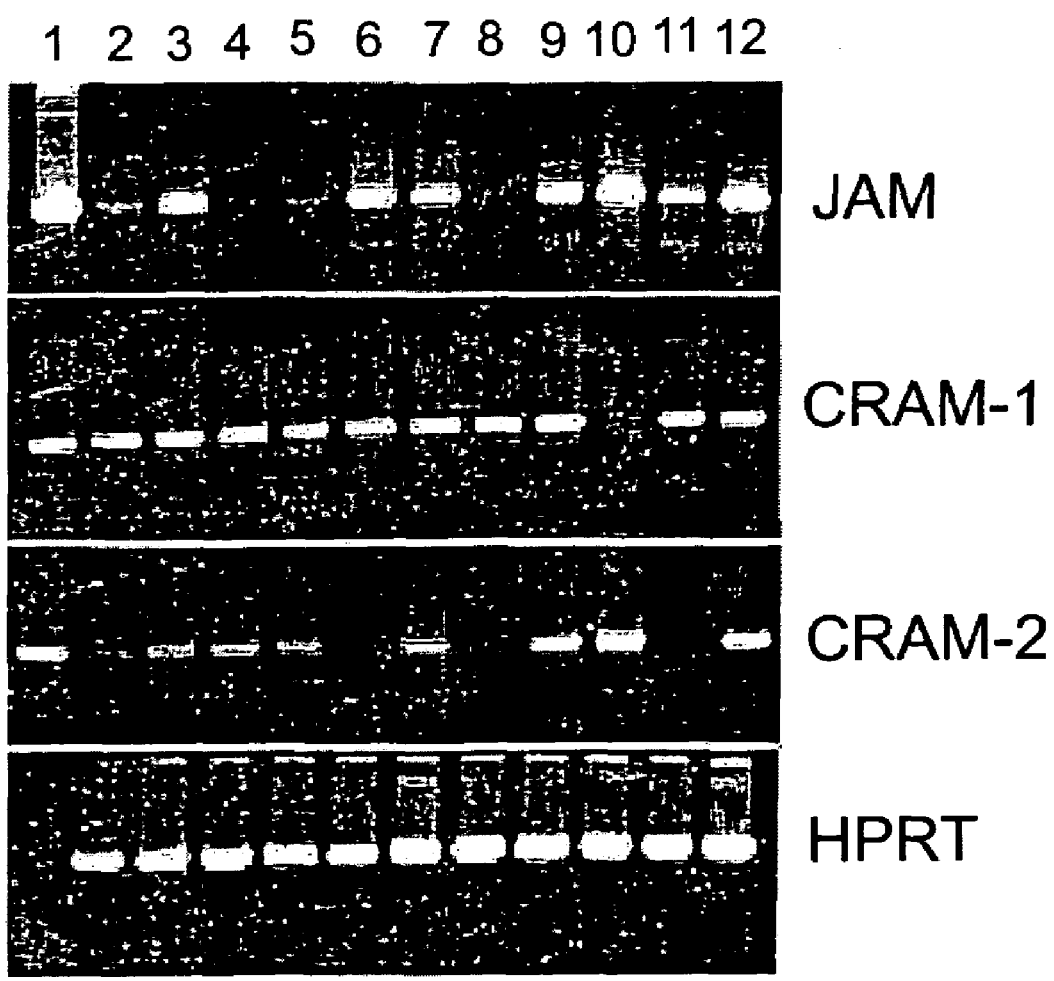

Expression of the three transcripts in cells of different origin was detected using RT-PCR. All endothelial, epithelial and most tumor cell lines tested, were positive, although at varying degrees for the different transcripts (FIG. 10A). The highest expression level for CRAM-1 was found in the SV40 transformed EV cell line (lane 9), and in the embryonic endothelial cell line e-end 2 (lane 4). The CRAM-2 and JAM transcripts showed a more restricted distribution, and were found in adult endothelial cell lines together with the CRAM-1 transcript (lanes 3, 7, 9 and 12). Notably, JAM and CRAM-2 transcripts were strongly downregulated by TNF treatment of endothelial cells whereas the level of CRAM-1 transcript remained unchanged (lanes 2 and 11). Interestingly, an embryonic endothelial cell line (lane 4) or an adult endothelial cell line representing an angiogenic variant of t-end (lane 6, failed to express JAM or CRAM-2.

The tissue distribution of JAM-2 transcript was explored by northern blotting and compared to JAM-1 (FIG. 14). The JAM-2 transcript was 2 kb long, highly expressed in embryonic tissue, and in Peyer's patches, lymph nodes, kidney, and testis of adult animals. A putative splice variant of 1.8 kb was detected in testis. Expression of JAM-2 transcript was low in lung, liver, spleen, and thymus. The relative abundance of JAM-1 and JAM-2 were compared during embryogenesis: the mRNA encoding JAM-2 was detectable as early as day 7.5 post coitum, whereas JAM-1 mRNA was not detected at all during embryogenesis.

These results suggest that CRAM-1 is widely expressed during embryogenesis and shows a restricted expression to epithelial or endothelial compartments in adult tissues. This is in agreement with the idea that it plays a role in the establishment and the maintenance of the polarized organization of cells.

Figure 11A:
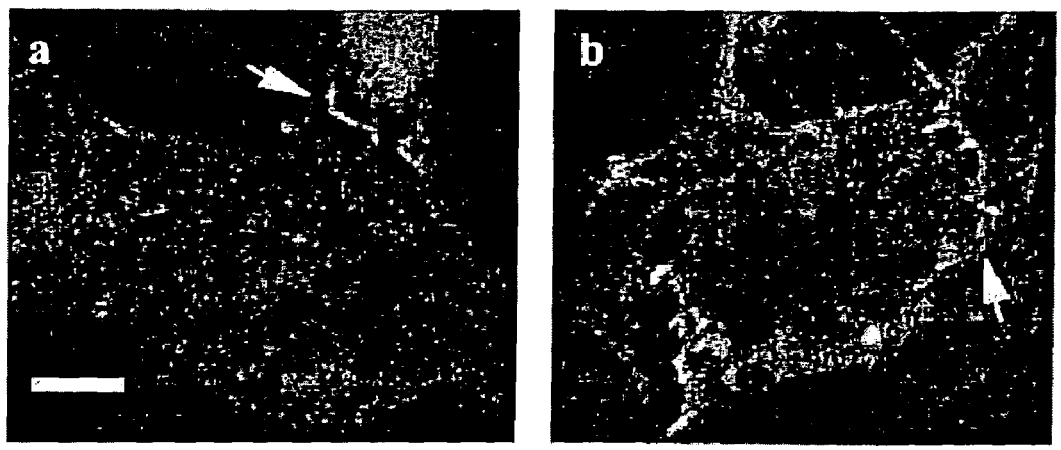

JAM-2, a 45 kD Protein, Depending on Homophilic Interactions for its Localization to Cell-Cell Contacts Since the HEV derived cell line TME expressed the highest level of JAM-2, this endothelial cell line was used to further study the subcellular localization of JAM-2, and to compare to that of JAM-1. The localization of the JAM-2 protein on the surface of the endothelial cells was restricted to cell-cell contacts (FIGS. 11A, a). The staining for JAM-2 was weaker than that observed for JAM-1 and less prominent in the membrane extensions between cells.

Figure 11B:

Then it was investigated whether JAM-2 present at cell-cell contacts interacted homophilically with JAM-2 or whether it interacted heterophilically with another molecule on the neighboring cell. For this purpose the JAM-2 protein was fused to green fluorescent protein (JAM-2-EGFP), and the construct transfected in CHO cells. When CHO cells transfected with JAM-2-EGFP cDNA reached confluency, JAM-2 was only observed in cell-cell contacts where both cells expressed the protein (FIG. 11B), whereas the contacts between expressing and non-expressing cells were devoid of JAM-2 (FIGS. 11B, a, indicated by arrow heads). The same result was obtained when cells were transfected with the chimeric molecule JAM-1-EGFP (FIGS. 11B, b). This indicated that either JAM-2, or JAM-1, needed homophilic interactions to be localized at cell-cell contacts.

Figure 11C:
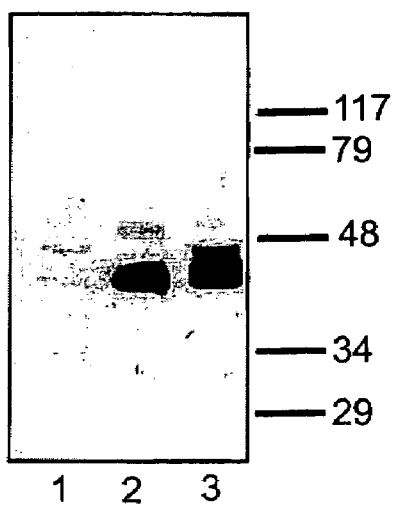

To characterize JAM-2 biochemically, immunoprecipitations of JAM-2 or EGFP chimeric proteins, expressed by TME cell line or by transfected CHO cells, respectively (FIGS. 11C and D) were performed. The anti-JAM-2 antibody, CRAM-19H36, immunoprecipitated a single band of 45 kD from TME cells lysate (FIG. 11C, lane 3).

The apparent molecular weight was identical under reducing or non-reducing conditions (not-shown) and corresponded to the predicted molecular weight deduced from the amino-acid sequence of JAM-2, each N-glycosylation site accounting for 5 kDa. Immunoprecipitation of JAM-1 using H202-106 anti-JAM specific antibody resulted in a single band of lower molecular weight (−42 kD, lane 2) that excluded a possible cross-reactivity between anti-JAM-2 and anti-JAM-1 antibodies.

Figure 11D:
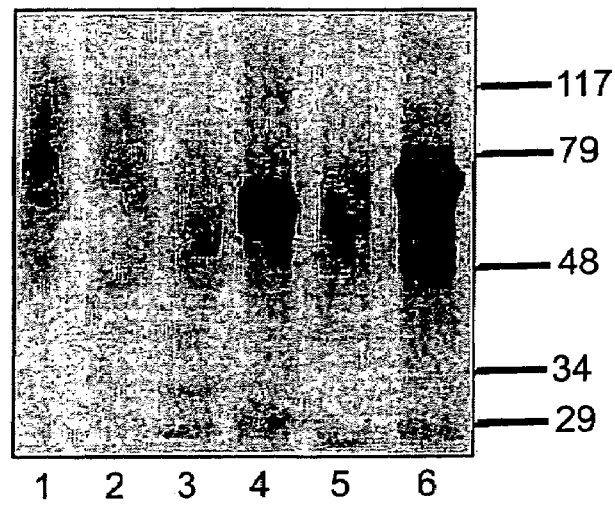

Immunoprecipitations of recombinant JAM-1-EGFP or JAM-2-EGFP proteins after surface biotinylation resulted in single broad bands of 70 and 73 kD respectively, indicating that the molecules were expressed on the surface of CHO transfected cells (FIG. 11D, lanes 4 and 6). These molecular weights were expected since EGFP has a molecular weight of 28 kD.

Tightness and Leukocyte Migration

Figure 20A:
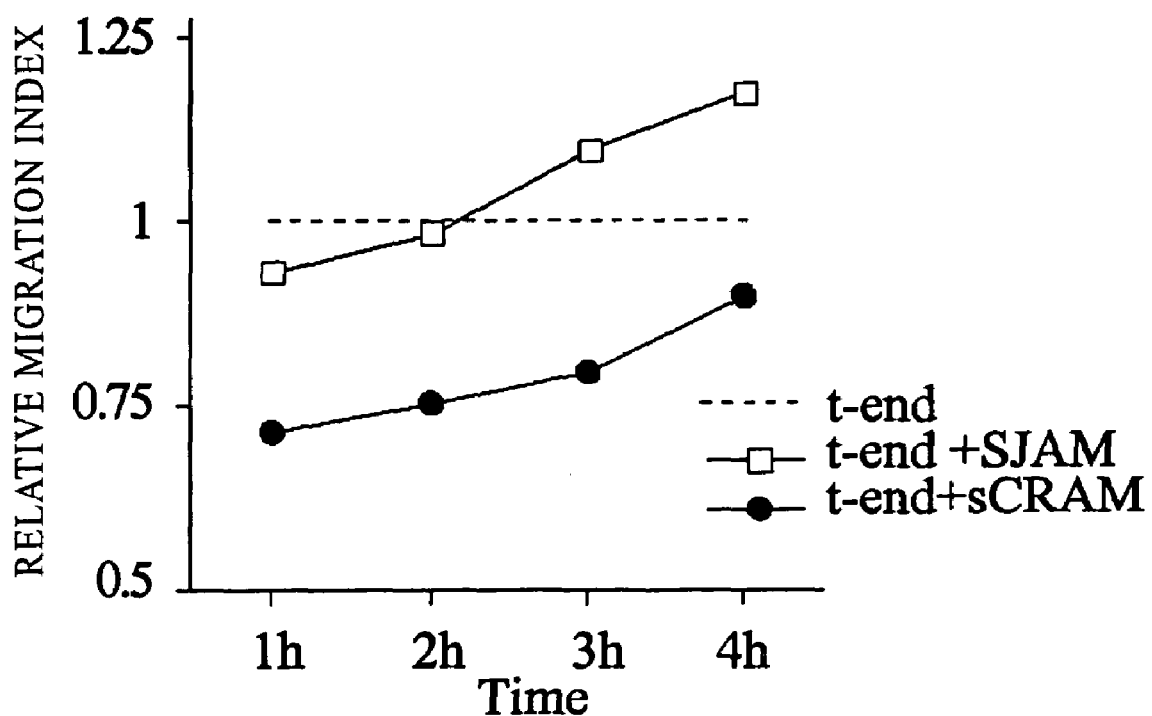

In order to understand how molecules influence the integrity of the endothelial cell monolayer and how they regulate the function of the vascular endothelium, leukocyte transendothelial migration assays were performed in the presence of recombinant soluble JAM or CRAM-1. Endothelial cells were cultured for two days in the presence of sJAM-Ig2Do or sCRAM-1-Ig2Do. The monolayer integrity was not affected during this period, probably due to the molecular redundancy of the mechanism of cell-cell contact formation. The transmigration assay was performed in the presence of 1 μg of recombinant soluble molecules. As shown in FIG. 20A, the number of transmigrating cells was poorly affected by the presence of sJAM-Ig2Do (open squares) during the first three hours. After four hours, the number of transmigrated cells increased when compared to the control (dashed line). In contrast, the presence of sCRAM-1-g2Do (closed circles) strongly reduced the number of transmigrating cells.

Figure 20B:
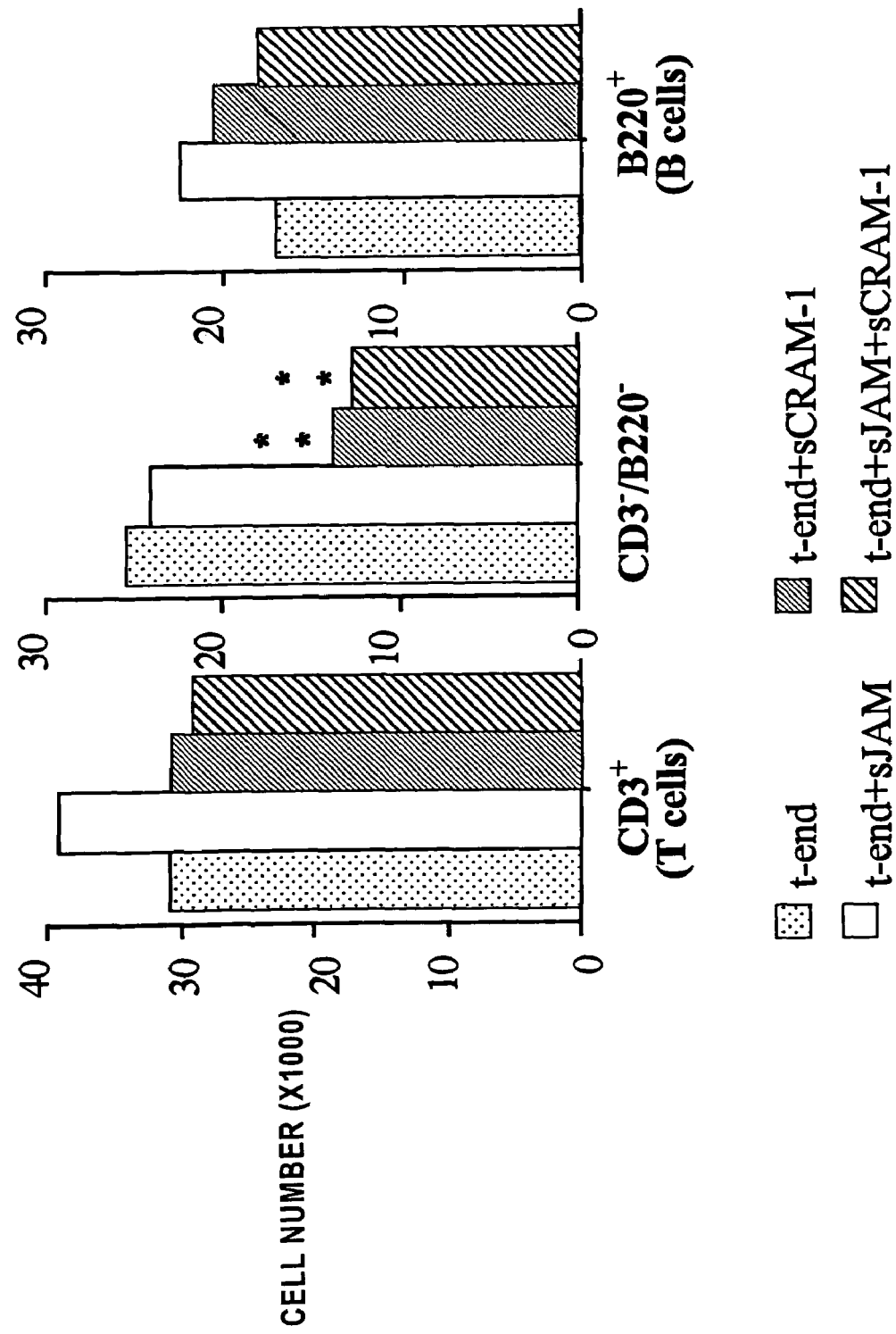

Since the leukocyte populations were heterogeneous, it was evaluated if sCRAM-1-Ig2Do acted on a specific leukocyte subpopulation or whether transmigration was blocked without specificity. For this purpose, the transmigrated cells were labeled for the lymphocyte markers CD3 and B220 (FIG. 20B).

Remarkably, sCRAM-1-Ig2Do specifically blocked the transmigration of non-lymphoid leukocytes, i.e. myeloid lineage cells (central panel, dashed columns). In contrast, sJAM-Ig2Do poorly increased the number of transmigrating T cells (left panel, white column) without any effect on other cell subpopulations.

Furthermore, when endothelioma cells transfected with CRAM-1 were used for transmigration assay, an increased transmigration was observed (FIG. 12), whereas the transfection of CRAM-2 was without effect on the transmigration. When SDF-1 was added to the assay, the leukocyte transendothelial migration reached 20%. This was partially blocked by monoclonal antibodies against CRAM-1.

These results indicate that the engagement of CRAM-1 between endothelial cells may regulate the function of the endothelial layer. It could be expected that the molecules of this family will become a barrier when endothelial cells reach confluency. To this end, the regulation of CRAM-1 transcripts was explored in endothelial cells under different culture conditions.

CRAM is Downregulated by High Confluence

Since the transcript that encodes CRAM-1 is not regulated by TNF, but is downregulated when the endothelium was co-cultured with tumor cells, a confluency assay was used to further explore this regulation. Under low confluency, the cells were actively cycling and CRAM-1 interactions did not occur whereas under high confluency the cells divided less and CRAM-1 was engaged. The level of CRAM-1 mRNA expression was determined under various cell densities by semi-quantitative RT-PCR. As shown in FIG. 13, the expression level of CRAM-1 transcripts decreased when confluency was reached (lanes 1, 2, 3 in FIG. 13 correspond to 100, 50, and 10% confluency respectively). This effect was hardly detectable with the t-end cells but was more pronounced with the TME cell line which highly expressed CRAM-1. The downregulation of CRAM-1 in endothelia was also enhanced when the endothelial cells were co-cultured with KLN 205 carcinoma cells which themselves do not express CRAM-1. This confirmed the link between CRAM-1 expression and the cell cycle since tumor cells were described to increase the growth rate of endothelial cells upon contact. It is noteworthy that the results obtained with KLN 205 carcinoma cells was identical to the one used in our original screening strategy with the B16 melanoma tumor. This indicates a general mechanism by which tumors affect endothelial behavior.

JAM-2 is Highly Expressed During Embryogenesis, and Restricted to HEVs and Endothelial Cells Subpopulations in Adult Tissues To better define the tissue distribution of JAM-2, immunohistological analysis was performed on kidney and mesenteric lymph node sections (FIG. 15), which expressed the highest levels of JAM-2 transcript. In the cortical region of the kidney, a specific staining of intertubular structures was detected with anti-PECAM (GC51) or anti-JAM-2 (CRAM-XVIIIF26) mAbs, whereas anti-ZO-1 or anti-JAM-1 stained predominantly the tubular epithelial cells (not shown).

The inventors therefore focused their attention on vascular structures, which dip down into the medulla and correspond to radial veins or vasa recta endothelial structures. For this purpose, serial sections were performed and the vascular structures identified with the anti-PECAM staining (FIG. 15d). On the equivalent region of neighboring sections, linear interendothelial stainings were detected with anti-JAM-2, anti-JAM-1 or anti-ZO-1 (FIGS. 15a, b and c, respectively). On sections of mesenteric lymph node, typical staining of high endothelial venules (HEVs) was obtained with anti-JAM-2 mAb (FIG. 15e). The HEVs were also found to express JAM-1, ZO-1 or PECAM (FIGS. 15f, g and h), with subtle differences in the subcellular localization of the stainings (FIG. 15e-h, insets). In the cortical area of the mesenteric lymph nodes, a typical staining of the subcapsular sinuses was observed with all antibodies (FIG. 15i-l), corresponding to the staining of afferent lymphatic vessels. Thus, the staining with the CRAM-18F26 anti-JAM-2 mAb is restricted to certain endothelial cells or to structures closely associated with vasculature.

Figure 16A:
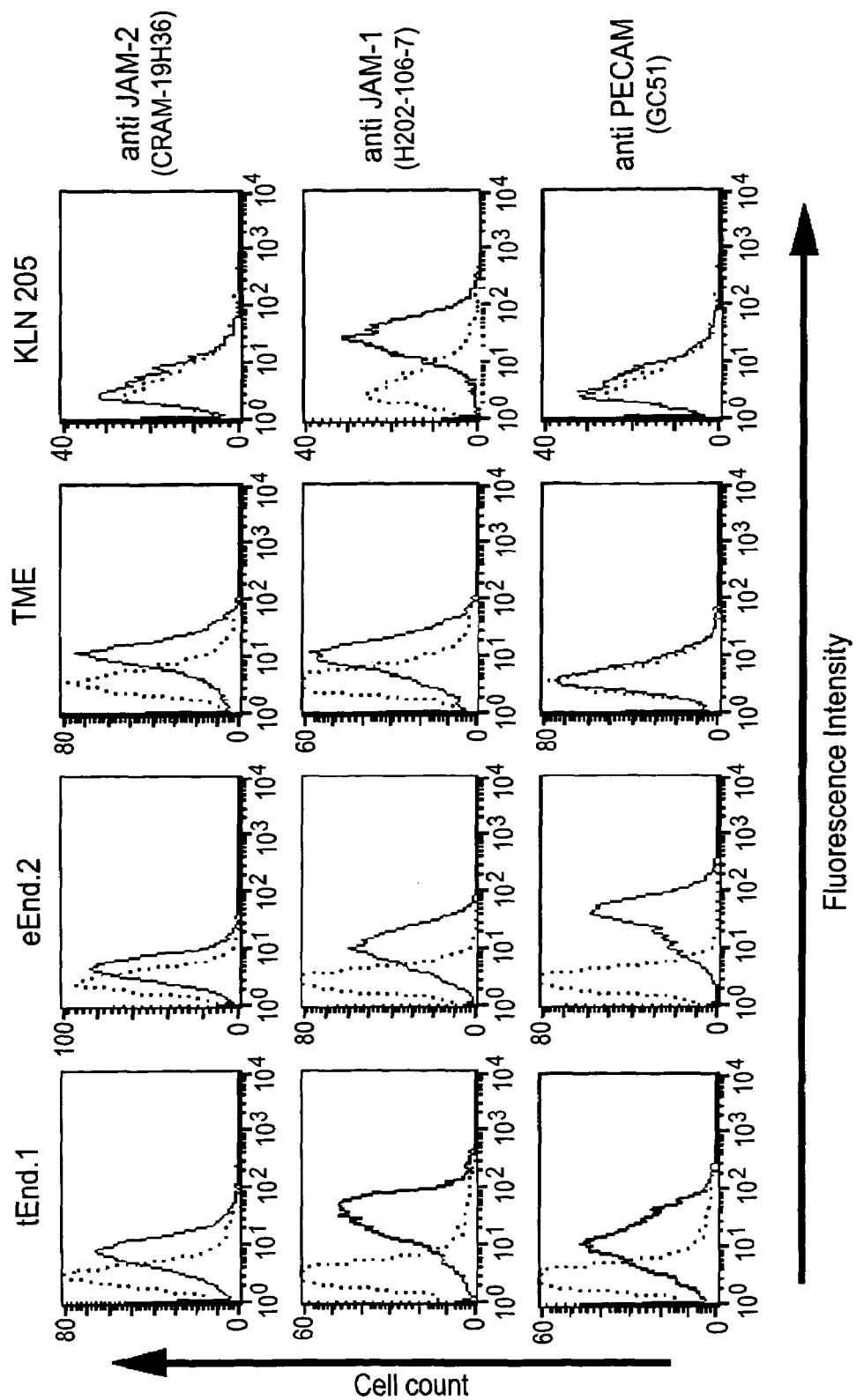

In order to clarify whether endothelial cells staining accounted for the pictures shown in FIG. 15, cytofluorimetry analysis of JAM-2 expression was performed on various cell lines or freshly isolated endothelial cells from dissociated tissues. Endothelial cell lines (tEnd.1, eEnd.2 and TME) expressed low levels of JAM-2 on the cell surface and variable levels of JAM-1 (FIG. 16A).

Figure 16B:
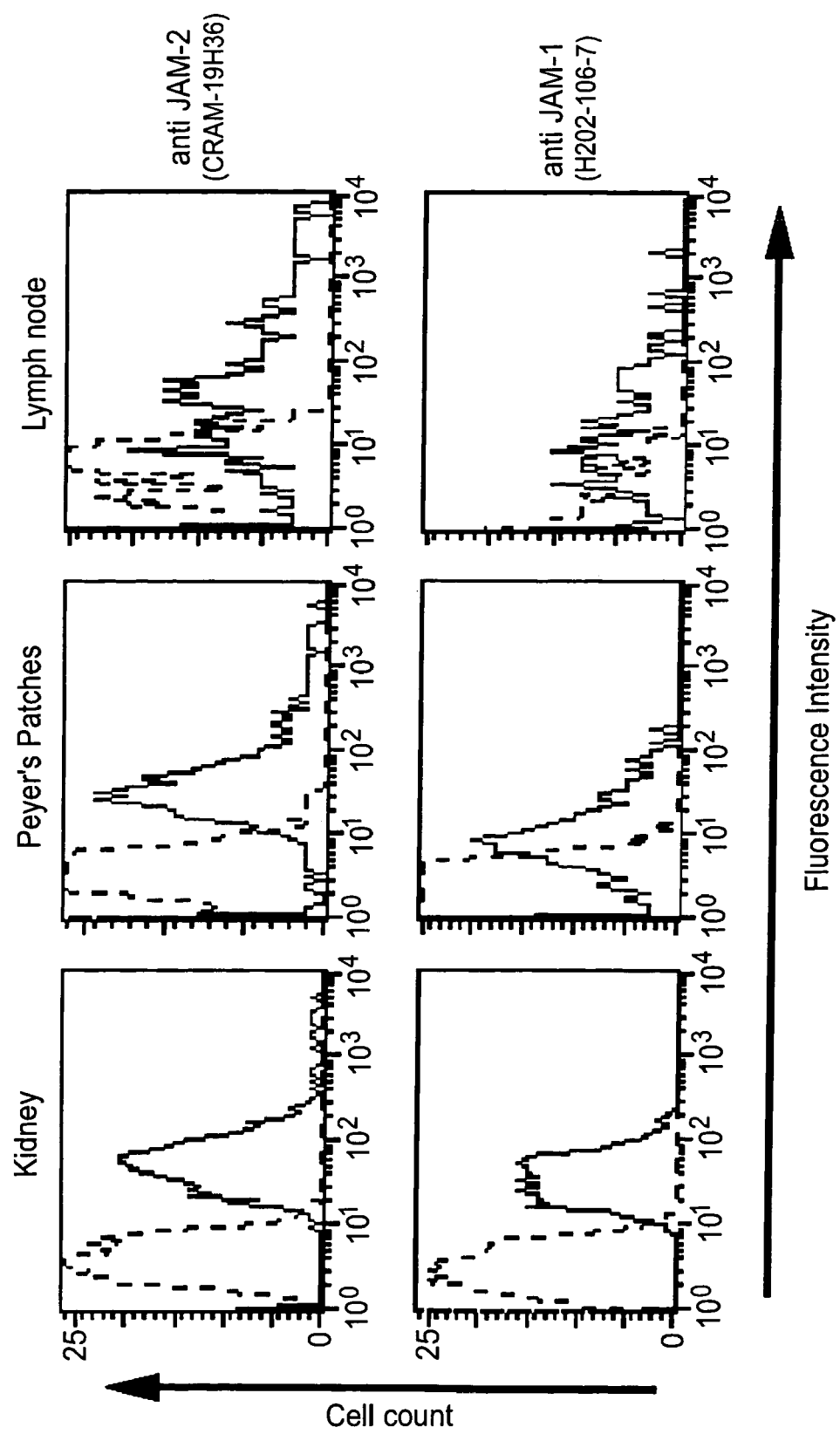

Cytometric analysis of freshly isolated endothelial cells was performed by triple staining of cell suspensions obtained after collagenase/dispase organ dissociation. Endothelial cells were identified by gating cells stained with both PECAM/CD31 and Acetylated-LDL (Voyta et al., 1984, *J. Cell Biol.* 99:2034). Staining for JAM-2 or JAM-1 on this double positive cell population is shown in FIG. 16B. In kidney and Peyer's patches, all the isolated cells positive for CD31 and Acetylated-LDL were also stained for JAM-2, meaning that, at least in these organs, endothelial cells expressed JAM-2 in vivo. When the staining was performed on cells obtained from lymph node, JAM-2 expression was only found on a cell subpopulation, reflecting a possible heterogeneity of endothelial cell phenotypes within this tissue.

Altogether, the results of cytometric and immunohistochemical analysis show that JAM-2 is co-expressed with JAM-1 by endothelial cells of kidney, Peyer's patches and lymph nodes.

Dynamic Localization of JAM-2 to Cell-Cell Contacts

Figure 17A:
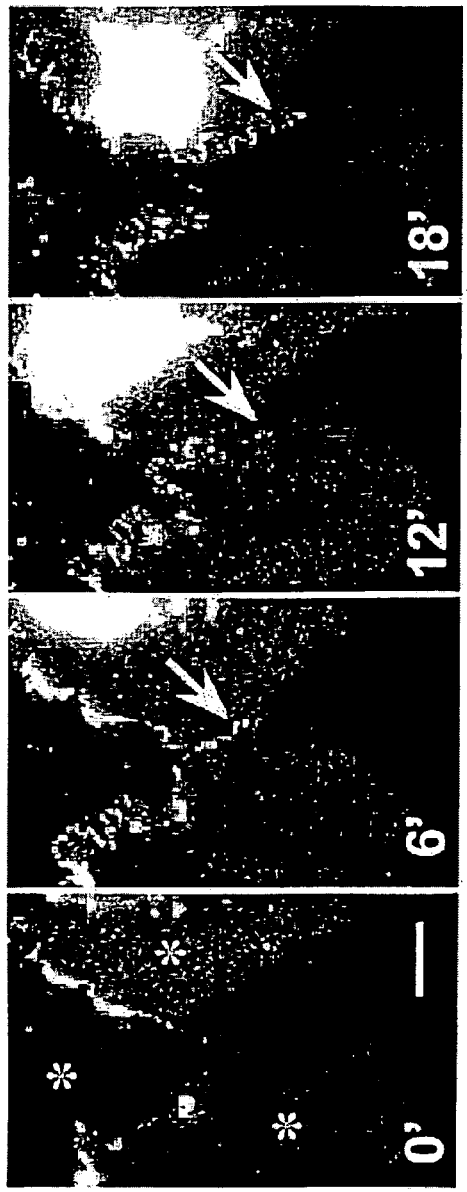

To dissect the mechanism by which JAM-2 was specifically localized to cell-cell contacts; time lapse video microscopy was used. The CHO cells, stably transfected with the fluorescent chimeric molecule, were trypsinized and plated into chamber slides for imaging. After cell spreading, surface expression of JAM-2-EGFP was not uniform but was rather clustered at cell-cell contacts (FIG. 17A, cells depicted by asterisks). During the formation of new cell-cell contacts, relocalization of JAM-2-EGFP to cell junctions was observed and an intense fluorescence signal was detected at the novel contact point between the cells forming the new cell-cell contact (arrows). The chimeric protein was enriched in the membrane protrusions between contacting cells, leading to the "zipper like" pictures seen after 12 or 16 min. Interestingly, the localization of JAM-2 at the primary cell-cell contacts was not lost during the formation of the new membrane contact (see upper left corner cell contacts). This finding indicated that JAM-2-EGFP was specifically relocalized to the new cell contact, and that, upon engagement, its localization was stable.

Figure 17B:
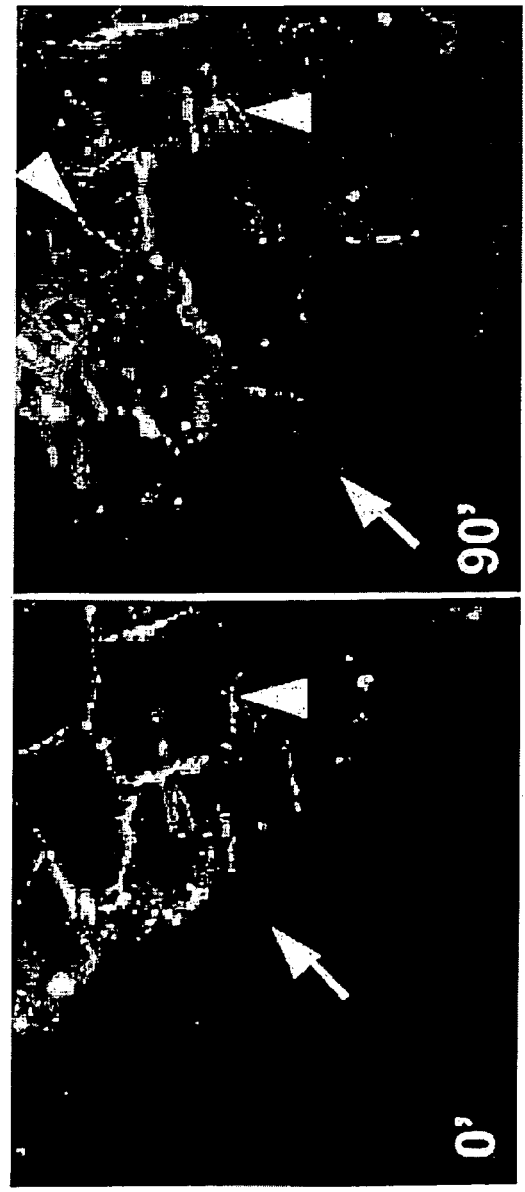

To further address the requirements for JAM-2 localization, time lapse video microscopy was performed after wounding the cell monolayer (FIG. 17B). Cells at the wounded edge maintained JAM-2 at their intact contact sites (arrowhead), but lost JAM-2 localization at the wounded side (arrows), indicating that JAM-2 engagement by a ligand on the opposing cell was necessary to maintain its membrane localization. Over a period of 90 min following wounding, cells bordering the wound began to migrate into the wounded area. Interestingly, these cells maintained contacts with neighboring cells via membrane protrusions that were brightly fluorescent, i.e JAM-2 positive (arrowhead). These results supported the hypothesis that CAM-2 homophilic interactions may play a role in the establishment or maintenance of cell-cell contacts.

JAM-2 Increases Monolayer Tightness and Participates to Tight Junctional Complexes Since a number of molecules participating in cell-cell connection, have been shown to regulate the paracellular permeability of cell monolayers, it was tested whether JAM-2 could also affect this function. Transfection of JAM-2-EGFP reduced the paracellular permeability to FITC dextran and improved sealing of CHO cell monolayers by 42.5%; whereas transfection of the unrelated molecule Tac (IL2R α), did not significantly reduce the paracellullar permeability of CHO transfected cells (FIG. 18). The transfection of JAM-1-EGFP also reduced the paracellular permeability of CHO transfected cells monolayer.

These results raised the question whether the chimeric molecules were able to participate to a subcellular specialized compartment such as tight junctions in polarized epithelial cells.

Figure 19A:
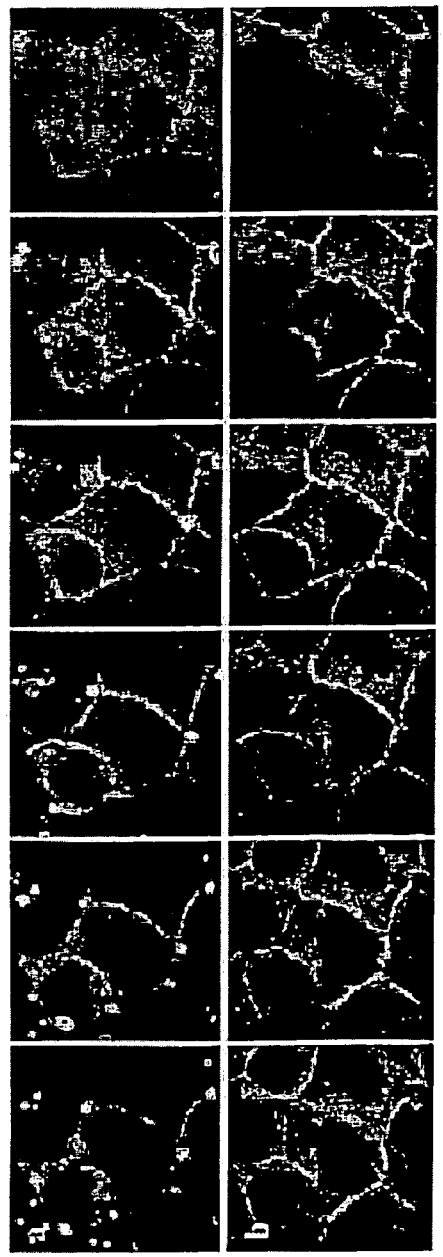
Figure 19B:
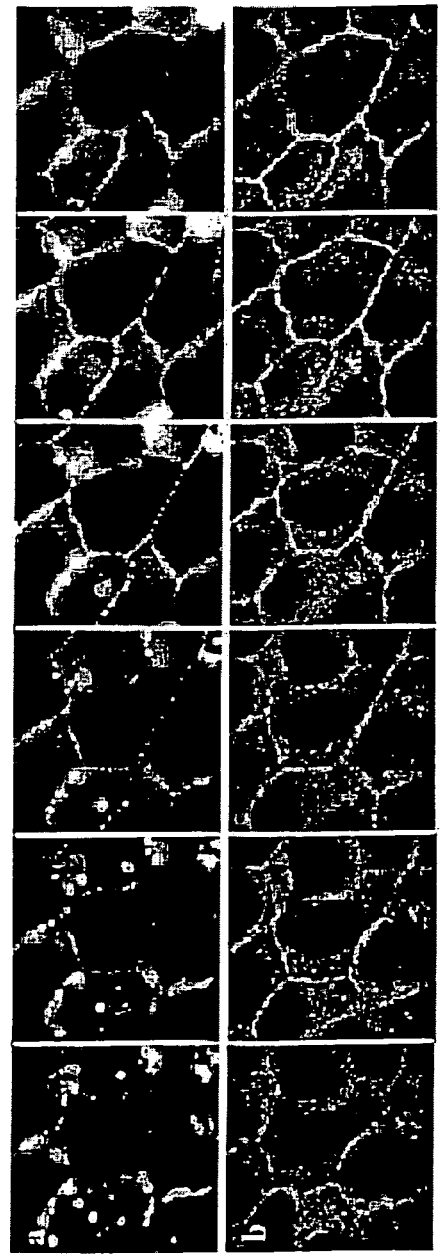

To answer this question, the EGFP chimeric proteins were transfected in MDCK cells, and their subcellular localization compared with that of the tight junctional marker: occludin. As shown in FIG. 19A, when serial pictures every 0.9 μm were analyzed for EGFP fluorescence and compared to occludin staining, JAM-2-EGFP was specifically enriched in cell-cell contacts at the level of tight junction. At the basal level (left), intracellular dots of EGFP fluorescence were observed. A similar analysis (FIG. 19B) of MDCK cells transfected with JAM-1-EGFP showed a similar co-localization with occludin. Nevertheless, the distribution of JAM-1-EGFP fluorescence was less continuous than that observed for JAM-2-EGFP at the level of tight junctions.

DISCUSSION

This example reports the use of a new screening strategy to identify regulated transcripts encoding members of the Ig superfamily of adhesion molecules. Described here is the cloning with this method of the new molecule CRAM-1 as a regulated transcript. The regulation observed in endothelial cells grown in the presence of tumors is confirmed by semi-quantitative RT-PCR and is shown to be dependant on the growth-phase of the cells. Due to differential expression under changing cell confluency conditions, the name CRAM-1 for "Confluency Regulated Adhesion Molecule-1" was adopted.

Also described herein is a closely related sequence to CRA-1 named CRAM-2 CRAM-1 and 2 represent the prototypes of a new subfamily of adhesion molecules which also includes the recently described molecule JAM (Chretien et al., 1998, Eur. J. Immunol. 28, 4094-4104; Malergue et al., 1998, Mol. Immunol. 35, 1111-1119).

CRAM-1 and JAM are preferentially expressed by endothelial and epithelial tissue at the cell-cell contacts and confer special properties to polarized layers. The effect of recombinant soluble molecules in a transendothelial migration assay and the regulation of JAM, CRAM-1 and CRAM-2 show that these three molecules play an important role in the maintenance of vascular physiology.

The new screening strategy, named Targeted Differential Display (TDD), has proved to be an efficient technique in selectively amplifying cDNA of interest. TDD successfully exploited the use of partially degenerated primers to confer selective targeting to the conserved region, Y(Y/Q/R)CXAS (SEQ ID NO:3 1), of C2 like Ig domains. Repeated experiments lead to reproducible display patterns. Out of 16 differentially expressed transcripts, three correspond to genes with significant homology to conserved Ig sequences. This increase in specificity manages to overcome the major difficulties in the already known techniques of classical RNA fingerprinting and differential display. RNA fingerprinting has long been used for the identification of differentially expressed genes, However, due to the sequence specific primers employed, this method detects only the transcripts of selected and already known proteins. On the other hand, RNA display employs random primers and involves the non-specific amplification of transcripts. The aim in this case is to pinpoint any differences in mRNA levels between two biological systems, which are submitted to comparison. TDD is an advanced screening method that combines the specificity of RNA fingerprinting with the degeneracy of Differential RNA Display resulting in selectivity. Due to the targeting of related transcripts, this technique significantly reduced the time needed for screening. The identification of new members of specific proteins families, therefore, becomes possible. This is a substantial improvement of the reported non-specific screening strategies.

These common features were used to construct recombinant proteins in order to study the functions of JAM, CRAM-1 and CRAM-2. In the present example, effects of sJAM-Ig2Do and sCRAM-1-Ig2Do are described in an vitro transmigration assay. Specific blocking effects on the migration of myeloid cells could be observed with sCRAM-1-Ig2Do whereas sJAM-Ig2Do showed only a small effect on lymphocytes.

JAM and CRAM-2 transcripts showed a similar tissue distribution and regulation of expression under the influence of TNF, indicating that they act by similar physiological mechanisms. In contrast, CRAM-1 transcripts are not regulated by TNF but rather by the rate of proliferation or the density of endothelial cells. In fact, overexpression of CRAM-1 transcripts in cycling cells and its downregulation in quiescent cells indicate that this molecule participates in the establishment of a continuous monolayer. Its function in confluent monolayers of cells is the maintenance of the endothelial cell layer and the related properties. Since different leukocyte populations have to migrate to the site of immune response, it is thought that non-lymphoid cells migrate via a CRAM-1 dependant mechanism, whereas lymphoid cells migrate via JAM or CRAM-2. In this case the immune response can be modulated by using combinations of different soluble recombinant molecules.

---

The invention claimed is:

1. An isolated polypeptide comprising:
   a) SEQ ID NO: 13;
   b) amino acids 1-291 of SEQ ID NO: 13; or
   c) the amino acid sequence encoded by:
      i) a nucleic acid encoding the amino acid sequence as set forth in SEQ ID NO:13;
      ii) a nucleic acid which hybridizes under highly stringent conditions to a nucleic acid that is the full complement of the nucleic acid encoding the amino acid sequence as set forth in SEQ ID NO:13, said highly stringent conditions include hybridization at 62° C. in buffer containing 50% formamide and a final wash at 67° C. in 0.5× SSC and 0.1% SDS and wherein said amino acid sequence increases transendothelial migration of leukocytes; or
      iii) a nucleic acid encoding a polypeptide comprising amino acids 1-291 of SEQ ID NO: 13.

2. The isolated polypeptide according to claim 1, wherein said polypeptide comprises the amino acid sequence of SEQ ID NO: 13.

3. The isolated polypeptide according to claim 1, wherein said polypeptide comprises amino acids 1-291 of SEQ ID NO: 13.

4. The isolated polypeptide according to claim 1, wherein said polypeptide comprises the amino acid sequence encoded by a nucleic acid, which hybridizes under highly stringent conditions to the full complement of a nucleic acid encoding the amino acid sequence as set forth in SEQ ID NO:13, said highly stringent conditions comprising hybridization at 62° C. in buffer containing 50% formamide and a final wash at 67° C. in 0.5× SSC and 0.1% SDS and wherein said amino acid sequence increases transendothelial migration of leukocytes.

5. A composition comprising:
   a) a polypeptide comprising SEQ ID NO: 13;
   b) a polypeptide comprising amino acids 1-291 of SEQ ID NO: 13; or
   c) the amino acid sequence encoded by:
      i) a nucleic acid encoding the amino acid sequence as set forth in SEQ ID NO: 13;
      ii) a nucleic acid which hybridizes under highly stringent conditions to a nucleic acid that is the full complement of the nucleic acid encoding the amino acid sequence as set forth in SEQ ID NO: 13, said highly stringent conditions include hybridization at 62° C. in buffer containing 50% formamide and a final wash at 67° C. in 0.5× SSC and 0.1% SDS and wherein said amino acid sequence increases transendothelial migration of leukocytes; or iii) a nucleic acid encoding a polypeptide comprising amino acids 1-291 of SEQ ID NO: 13.

6. The composition according to claim 5, wherein said polypeptide comprises the amino acid sequence of SEQ ID NO: 13.

7. The composition according to claim 5, wherein said polypeptide comprises amino acids 1-291 of SEQ ID NO: 13.

8. The composition according to claim 5, wherein said polypeptide comprises the amino acid sequence encoded by a nucleic acid, which hybridizes under highly stringent conditions to the full complement of a nucleic acid encoding the amino acid sequence as set forth in SEQ ID NO: 13, said highly stringent conditions comprising hybridization at 62° C. in buffer containing 50% formamide and a final wash at 67° C. in 0.5× SSC and 0.1% SDS and wherein said amino acid sequence increases transendothelial migration of leukocytes.

9. An isolated polypeptide comprising:
  a) amino acids 1-159 of SEQ ID NO: 13, wherein said polypeptide inhibits transendothelial migration of leukocytes;
  b) amino acids 25-241 of SEQ ID NO: 13, wherein said polypeptide inhibits transendothelial migration of leukocytes;
  c) amino acids 1-238 of SEQ ID NO: 13, wherein said polypeptide inhibits transendothelial migration of leukocytes; or
  d) the amino acid sequence encoded by a nucleic acid which hybridizes under highly stringent conditions to a nucleic acid that is the full complement of the nucleic acid encoding amino acids 1-159 of SEQ ID NO: 13, amino acids 25-241 of SEQ ID NO: 13, or amino acids 1-238 of SEQ ID NO: 13, said highly stringent conditions include hybridization at 62° C. in buffer containing 50% formamide and a final wash at 67° C. in 0.5× SSC and 0.100 SDS and wherein said amino acid sequence inhibits transendothelial migration of leukocytes.

10. The isolated polypeptide according to claim 9, wherein said isolated polypeptide comprises amino acids 1-159 of SEQ ID NO: 13 and inhibits transendothelial migration of leukocytes.

11. The isolated polypeptide according to claim 9, wherein said isolated polypeptide comprises amino acids 25-241 of SEQ ID NO: 13 and said polypeptide inhibits transendothelial migration of leukocytes.

12. The isolated polypeptide according to claim 9, wherein said isolated polypeptide comprises amino acids 1-238 of SEQ ID NO: 13 and said polypeptide inhibits transendothelial migration of leukocytes.

13. An isolated fusion protein comprising:
  a) amino acids 25-241 of SEQ ID NO:13;
  b) amino acids 1-159 of SEQ ID NO: 13; or
  c) amino acids 1-238 of SEQ ID NO: 13;
wherein said fusion protein inhibits transendothelial migration of leukocytes.

14. The isolated fusion protein according to claim 13, wherein said fusion protein comprises amino acids 1-159 of SEQ ID NO: 13 and said fusion protein inhibits transendothelial migration of leukocytes.

15. The isolated fusion protein according to claim 13, wherein said fusion protein comprises amino acids 25-241 of SEQ ID NO: 13 and said fusion protein inhibits transendothelial migration of leukocytes.

16. The isolated fusion protein according to claim 13, wherein said fusion protein comprises amino acids 1-238 of SEQ ID NO: 13 and said fusion protein inhibits transendothelial migration of leukocytes.

17. A composition comprising:
  a) an isolated polypeptide comprising amino acids 1-159 of SEQ ID NO: 13, wherein said polypeptide inhibits transendothelial migration of leukocytes;
  b) an isolated polypeptide comprising amino acids 25-241 of SEQ ID NO: 13, wherein said polypeptide inhibits transendothelial migration of leukocytes;
  c) an isolated polypeptide comprising amino acids 1-238 of SEQ ID NO: 13, wherein said polypeptide inhibits transendothelial migration of leukocytes; or
  d) an isolated polypeptide comprising the amino acid sequence encoded by a nucleic acid which hybridizes under highly stringent conditions to a nucleic acid that is the full complement of the nucleic acid encoding amino acids 1-159 of SEQ ID NO: 13, amino acids 25-241 of SEQ ID NO: 13, or amino acids 1-238 of SEQ ID NO: 13, said highly stringent conditions include hybridization at 62° C. in buffer containing 50% formamide and a final wash at 67° C. in 0.5× SSC and 0.1% SDS and wherein said amino acid sequence inhibits transendothelial migration of leukocytes.

18. The composition according to claim 17, wherein said isolated polypeptide comprises amino acids 1-159 of SEQ ID NO: 13 and inhibits transendothelial migration of leukocytes.

19. The composition according to claim 17, wherein said isolated polypeptide comprises amino acids 25-241 of SEQ ID NO: 13 and inhibits transendothelial migration of leukocytes.

20. The composition according to claim 17, wherein said isolated polypeptide comprises amino acids 1-238 of SEQ ID NO: 13 and inhibits transendothelial migration of leukocytes.

21. A composition comprising a fusion protein comprising:
  a) a polypeptide comprising amino acids 25-241 of SEQ ID NO: 13;
  b) a polypeptide comprising amino acids 1-159 of SEQ ID NO: 13; or
  c) a polypeptide comprising amino acids 1-238 of SEQ ID NO: 13;
wherein said fusion protein inhibits transendothelial migration of leukocytes.

22. The composition according to claim 21, wherein said fusion protein comprises amino acids 1-159 of SEQ ID NO: 13 and said fusion protein inhibits transendothelial migration of leukocytes.

23. The composition according to claim 21, wherein said fusion protein comprises amino acids 25-241 of SEQ ID NO: 13 and said fusion protein inhibits transendothelial migration of leukocytes.

24. The composition according to claim 21, wherein said fusion protein comprises amino acids 1-238 of SEQ ID NO: 13 and said fusion protein inhibits transendothelial migration of leukocytes.

25. The isolated polypeptide according to claim 9, wherein said polypeptide is the amino acid sequence encoded by a nucleic acid which hybridizes under highly stringent conditions to a nucleic acid that is the full complement of the nucleic acid encoding amino acids 1-159 of SEQ ID NO: 13, said highly stringent conditions include hybridization at 62° C. in buffer containing 50% formamide and a final wash at 67° C. in 0.5× SSC and 0.1% SDS and wherein said amino acid sequence inhibits transendothelial migration of leukocytes.

26. The isolated polypeptide according to claim 9, wherein said polypeptide is the amino acid sequence encoded by a nucleic acid which hybridizes under highly stringent conditions to a nucleic acid that is the full complement of the nucleic acid encoding amino acids 25-241 of SEQ ID NO: 13, said highly stringent conditions include hybridization at 62° C. in buffer containing 50% formamide and a final wash at 67° C. in 0.5× SSC and 0.1% SDS and wherein said amino acid sequence inhibits transendothelial migration of leukocytes.

27. The isolated polypeptide according to claim 9, wherein said polypeptide is the amino acid sequence encoded by a nucleic acid which hybridizes under highly stringent conditions to a nucleic acid that is the full complement of the nucleic acid encoding amino acids 1-238 of SEQ ID NO: 13, said highly stringent conditions include hybridization at 62° C. in buffer containing 50% formamide and a final wash at 67° C. in 0.5× SSC and 0.1% SDS and wherein said amino acid sequence inhibits transendothelial migration of leukocytes.

28. The composition according to claim 17, wherein said isolated polypeptide is the amino acid sequence encoded by a nucleic acid which hybridizes under highly stringent conditions to a nucleic acid that is the full complement of the nucleic acid encoding amino acids 1-159 of SEQ ID NO: 13, said highly stringent conditions include hybridization at 62° C. in buffer containing 50% formamide and a final wash at 67° C. in 0.5× SSC and 0.1% SDS and wherein said amino acid sequence inhibits transendothelial migration of leukocytes.

29. The composition according to claim 17, wherein said isolated polypeptide is the amino acid sequence encoded by a nucleic acid which hybridizes under highly stringent conditions to a nucleic acid that is the full complement of the nucleic acid encoding amino acids 25-241 of SEQ ID NO: 13, said highly stringent conditions include hybridization at 62° C. in buffer containing 50% formamide and a final wash at 67° C. in 0.5× SSC and 0.1% SDS and wherein said amino acid sequence inhibits transendothelial migration of leukocytes.

30. The composition according to claim 17, wherein said polypeptide is the amino acid sequence encoded by a nucleic acid which hybridizes under highly stringent conditions to a nucleic acid that is the full complement of the nucleic acid encoding amino acids 1-238 of SEQ ID NO: 13, said highly stringent conditions include hybridization at 62° C. in buffer containing 50% formamide and a final wash at 67° C. in 0.5× SSC and 0.1% SDS and wherein said amino acid sequence inhibits transendothelial migration of leukocytes.

* * * * *

UNITED STATES PATENT AND TRADEMARK OFFICE
CERTIFICATE OF CORRECTION

| | | |
|---|---|---|
| PATENT NO. | : 7,393,651 B2 | |
| APPLICATION NO. | : 11/025834 | |
| DATED | : July 1, 2008 | |
| INVENTOR(S) | : Beat Albert Imhof and Michel Aurrand-Lions | |

It is certified that error appears in the above-identified patent and that said Letters Patent is hereby corrected as shown below:

Column 4,
Line 67, "17 and T3" should read --T7 and T3--.

Column 5,
Line 27, "and taytaytaynnnacyagyaa" should read --and taytaytgynnngcyagyaa--.
Line 65, "(B) (A):" should read --(B). (A):--.

Column 6,
Line 61, "PECAN" should read --PECAM--.

Column 7,
Line 23, "Transfcction of" should read --Transfection of--.
Line 23, "JAM-1-EGPP" should read --JAM-1-EGFP--.
Line 43, "sJAM-I2do" should read --sJAM-Ig2do--.

Column 8,
Line 26, "IIPRT cDNA" should read --HPRT cDNA--.
Line 34, "gf using" should read --of using--.

Column 9,
Line 6, "Gibco ORL" should read --Gibco BRL--.
Lines 51-64, "As internal control, the following primers specific for Hprt cDNA were used to amplify a 350 bp long fragment: 5'-GTTGGATACAGGCCAGACTTTGTTG-3' (SEQ ID NO:9) and 5'-GAGGGTAGGCTGGCCTATAGGCT-3' (SEQ ID NO:10).

5'-GTTGGATACAGGCCAGACTTTGTTG-3' (SEQ ID NO:9) and 5' -
    5'-GAGGGTAGGCTGGCCTATAGGCT-3' (SEQ ID NO:10).

Construction of Expression Vectors"

should read

--As internal control, the following primers specific for Hprt cDNA were used to amplify a 350 bp long fragment: 5'-GTTGGATACAGGCCAGACTTTGTTG-3' (SEQ ID NO:9) and 5'-GAGGGTAGGCTGGCCTATAGGCT-3' (SEQ ID NO:10).

Construction of Expression Vectors--.

UNITED STATES PATENT AND TRADEMARK OFFICE
CERTIFICATE OF CORRECTION

PATENT NO.        : 7,393,651 B2
APPLICATION NO.   : 11/025834
DATED             : July 1, 2008
INVENTOR(S)       : Beat Albert Imhof and Michel Aurrand-Lions It is certified that error appears in the above-identified patent and that said Letters Patent is hereby corrected as shown below:

Column 10,
Line 37, "3+" should read --3'--.
Line 37, "Bite" should read --site--.
Line 47, "GC51, rat $IgG_{1a}$" should read --GC51, rat $IgG_{2a}$--.

Column 12,
Line 16, "sCRAM-2do" should read --sCRAM-1 2do--.
Line 62, "SEO ID NO:20" should read --SEQ ID NO:20--.

Column 13,
Line 9, "(SEQ ID) NO:20)" should read --(SEQ ID NO:20)--.
Line 36, "chain arid" should read --chain and--.
Line 44, "SSKISYK" should read --SSK/SYK--.

Column 14,
Line 9, "transformed EV" should read --transformed HEV--.

Column 16,
Line 45, "(FIGS. 15f, g and b)" should read --(FIGS. 15f, g and h)--.

Column 17,
Line 28, "12 or 16" should read --12 or 18--.
Line 47, "CAM-2" should read --JAM-2--.

UNITED STATES PATENT AND TRADEMARK OFFICE
CERTIFICATE OF CORRECTION

PATENT NO. : 7,393,651 B2
APPLICATION NO. : 11/025834
DATED : July 1, 2008
INVENTOR(S) : Beat Albert Imhof and Michel Aurrand-Lions It is certified that error appears in the above-identified patent and that said Letters Patent is hereby corrected as shown below:

Column 18,
Line 31, "CRA-1 named CRAM-2 CRAM-1 and 2" should read
--CRAM-1 named CRAM-2. CRAM-1 and -2--.
Line 48, "(SEQ ID NO: 3 1)" should read --(SEQ ID NO:31)--.
Line 56, "genes, However," should read --genes. However--.

Column 43,
Line 38, "0.100 SDS" should read --0.1% SDS--.

Signed and Sealed this

Ninth Day of December, 2008

JON W. DUDAS
*Director of the United States Patent and Trademark Office*